(12) United States Patent
Mes et al.

(10) Patent No.: US 11,884,781 B2
(45) Date of Patent: Jan. 30, 2024

(54) SUPRAMOLECULAR BIOMEDICAL POLYMERS

(71) Applicant: SupraPolix B.V., Eindhoven (NL)

(72) Inventors: Tristan Mes, Eindhoven (NL); Anton Willem Bosman, Eindhoven (NL); Joris Wilhelmus Peeters, Horn (NL); Henricus Marie Janssen, Eindhoven (NL)

(73) Assignee: SUPRAPOLIX B.V., Eindhoven (NL)

( * ) Notice: Subject to any disclaimer, the term of this patent is extended or adjusted under 35 U.S.C. 154(b) by 174 days.

(21) Appl. No.: 16/877,980

(22) Filed: May 19, 2020

(65) Prior Publication Data

US 2020/0277448 A1 Sep. 3, 2020

Related U.S. Application Data

(63) Continuation of application No. PCT/NL2018/050780, filed on Nov. 21, 2018.

(30) Foreign Application Priority Data

Nov. 22, 2017 (NL) ..................................... 2019957

(51) Int. Cl.
| | | |
|---|---|---|
| *A61L 27/18* | (2006.01) | |
| *A61L 27/58* | (2006.01) | |
| *C08G 18/10* | (2006.01) | |
| *C08G 18/12* | (2006.01) | |
| *C08G 18/32* | (2006.01) | |
| *C08G 18/38* | (2006.01) | |
| *C08G 18/42* | (2006.01) | |
| *C08G 18/66* | (2006.01) | |
| *C08G 18/73* | (2006.01) | |
| *C08G 83/00* | (2006.01) | |
| *C08L 101/00* | (2006.01) | |
| *A61L 27/56* | (2006.01) | |
| *A61L 31/06* | (2006.01) | |
| *A61L 31/14* | (2006.01) | |

(52) U.S. Cl.
CPC ............ *C08G 83/008* (2013.01); *A61L 27/18* (2013.01); *A61L 27/56* (2013.01); *A61L 27/58* (2013.01); *A61L 31/06* (2013.01); *A61L 31/146* (2013.01); *A61L 31/148* (2013.01); *C08G 18/3206* (2013.01); *C08G 18/73* (2013.01); *C08G 2230/00* (2013.01)

(58) Field of Classification Search
CPC .. C08G 83/008; C08G 18/3206; C08G 18/73; C08G 2230/00; C08G 18/44; C08G 64/42; C08G 18/0852; C08G 18/244; C08G 18/3848; C08G 18/4854; C08G 18/6208; C08G 18/6651; C08G 18/69; A61L 27/18; A61L 27/56; A61L 27/58; A61L 31/06; A61L 31/146; A61L 31/148; C08L 101/00; D01D 5/0038; D01F 6/70
See application file for complete search history.

(56) References Cited

U.S. PATENT DOCUMENTS

| | | | | |
|---|---|---|---|---|
| 6,136,333 | A * | 10/2000 | Cohn | .................. C08G 63/664 424/78.17 |
| 6,320,018 | B1 | 11/2001 | Sijbesma et al. | |
| 10,358,522 | B2 * | 7/2019 | Mes | ...................... C08G 18/10 |
| 10,941,239 | B2 * | 3/2021 | Mes | ...................... C08G 18/12 |
| 2004/0087755 | A1 | 5/2004 | Eling et al. | |
| 2008/0260795 | A1 | 10/2008 | Baughman et al. | |
| 2009/0130172 | A1 | 5/2009 | Dankers et al. | |
| 2012/0116014 | A1 | 5/2012 | Janssen et al. | |
| 2016/0115272 | A1 * | 4/2016 | Mes | ................... C08L 101/005 528/73 |

FOREIGN PATENT DOCUMENTS

| | | |
|---|---|---|
| EP | 1 511 764 A2 | 3/2005 |
| EP | 1 511 794 A2 | 3/2005 |
| EP | 2 450 394 A1 | 5/2012 |
| WO | WO-03/099875 A1 | 12/2003 |
| WO | WO-2005/042641 A1 | 5/2005 |
| WO | WO-01/4007631 A1 | 1/2014 |
| WO | WO-01/4185779 A1 | 11/2014 |

OTHER PUBLICATIONS

Kidane et al. Acta Biomaterialia 5 (2009) 2409-2417 (Year: 2009).*
Ma et al. Biomacromolecules 2011, 12, 9, 3265-3274 (Year: 2011).*
Radhakrishnan et al. RSC Adv., 2014, 4, 15087-15090 (Year: 2014).*
Ulery et al. Journal of Polymer Science Part B: Polymer Physics 2011, 49, 832-864. (Year: 2011).*
Zhu et al. .Appl. Sci. 2017, 7, 306. (Year: 2017).*
International Search Report dated Apr. 11, 2019 in corresponding International Application No. PCT/NL2018/050780, 4 pages.

* cited by examiner

*Primary Examiner* — Mina Haghighatian
*Assistant Examiner* — Janice Y Silverman
(74) *Attorney, Agent, or Firm* — Sunit Talapatra; Foley & Lardner LLP

(57) ABSTRACT

The present invention relates to supramolecular biomedical polymers comprising quadruple hydrogen bonding units and to a process for preparing such a supramolecular biomedical polymer and porous biomedical implants thereof. The supramolecular biomedical polymers are particularly suitable for the production of porous biomedical implants that need high strength, elasticity, durability, and slow biodegradation, e.g. medical implants for living tissue regeneration within a mammal, such as the treatment of cardio-vascular diseases, medical prolapses, and hernias.

19 Claims, No Drawings

SUPRAMOLECULAR BIOMEDICAL POLYMERS

CROSS-REFERENCE TO RELATED APPLICATIONS

This application is a continuation of International Application No. PCT/NL2018/050780, filed Nov. 21, 2018, which claims the benefit of and priority to Netherlands Application No. 2019957, filed Nov. 22, 2017, both of which are hereby incorporated by reference herein in their entireties.

FIELD OF THE INVENTION

The present invention relates to a process for the manufacture of supramolecular polymers and to the supramolecular polymers that are obtained via said process. The present invention further relates to porous biomedical implants comprising said supramolecular polymers, their production, and their use in medical methods of treatment, such as in the treatment of cardio-vascular diseases in a mammal and in the treatment of a medical condition requiring reconstruction surgery, support or augmentation of mammalian tissue.

BACKGROUND OF THE INVENTION

A wide variety of biodegradable (also often designated as bioresorbable or biomedical) materials are known that are mostly based on aliphatic polyesters such as polycaprolactone and their copolymers (Uhrich et al., *Chem. Rev.* 99, 3181-3198, 1999). In the context of the present invention, the terms 'biomedical', 'bioresorbable', and 'biodegradable' have the same meaning and are considered interchangeable. The mechanical properties of current biodegradable materials are strongly related to their high molecular weights that are in general over 100 kDa, the presence of chemical cross-links, and the presence of crystalline 'hard' domains in these polymers. Although the crystalline domains are beneficial for the initial high strength of the material, they do have a strong impact on the biodegradation process of the material as the biodegradation of crystalline domains is in general very slow and, moreover, because these crystalline domains may cause immunological responses. Additionally, the crystalline domains may have a negative impact on the long term elastic behaviour of the material due to their tendency to induce fatigue characteristics.

The need for high molecular weight polymers, in order to get the desired material properties, usually implies that high processing temperatures are required which are unfavourable as thermal degradation processes become more likely at high temperatures.

Moreover, the presence of ester-linkages in biodegradable materials comprising polyesters, such as polycaprolactones, makes them prone to (enzymatic) hydrolysis and therefore premature failure of biomedical implants, i.e. biodegradable implants for use inside the human or animal body, comprising these polymers. In other words, biodegradable materials comprising polyesters may have such a fast biodegradability that they are not suitable for use in biomedical implants.

The mechanical performance needed for a biomedical implant depends on the intended site of implantation in the body. Flexible implants are needed when the site of implantation is for example an abdominal wall, a cardio-vascular site, an organ or skin. Typical elongations that occur in the abdominal wall of humans are on average 32% with extremes towards 69% for women. A Young's modulus in the range of 5-10 MPa is typically found in the abdominal walls of animals (Deeken et al., *J. Mech. Behav. Biomed. Mat.* 74, 411, 2017; incorporated herein by reference). Elastic moduli found in the leaflets of human heart valves have values up to 10-14 MPa with maximum strains up to 30% and ultimate tensile strengths of 2-4 MPa (Stradins et al., *Eur. J Cardio-Thorac. Surg.* 26, 634, 2004 and Hasan et al., *J Biomech* 47, 1949, 2014; incorporated herein by reference). The mechanical behaviour of human skin is characterized by an average elastic modulus of 83 MPa, an ultimate tensile strength of around 22 MPa with elongations up to 170% (Annaish et al., *J. Mech. Behav. Biomed. Mat.* 5, 139, 2012; incorporated herein by reference).

Durability of a biomedical implant is also crucial for its performance since the biomedical implant needs to be able to withstand millions of movements during its lifetime such that its fatigue resistance should be high. For example, heart valves undergo a complex cyclic loading with a high mechanical demand of around 30 million times a year, thereby pumping 3-5 L of blood through the valves every minute (see Hasan et al., *J Biomech* 47, 1949, 2014).

Another important parameter for the performance of a biomedical implant is its deformation behaviour, which is the mechanical response of the biomedical implant towards stress or elongation. This is in flexible soft tissues often non-linear and characterized by a high ultimate tensile strength combined with low initial stress at low elongations (Mazza et al., *J. Mech Behav. Biomed. Mat.* 48, 100, 2015; incorporated herein by reference).

If the biomedical implant is a porous implant, the polymer that constitutes this biomedical implant needs to display even higher elastic moduli and tensile strengths to counterbalance the decrease in mechanical performance of the biomedical implant due to the porosity.

The present invention relates to supramolecular biomedical polymers that comprise moieties that are capable of forming at least four H-bridges in a row, preferably with another moiety capable of forming at least four H-bridges in a row, leading to physical interactions between different polymer chains. The physical interactions originate from multiple hydrogen bonding interactions, also called supramolecular interactions, between individual moieties that are capable of forming at least four H-bridges in a row or between a moiety capable of forming at least four H-bridges in a row and another moiety capable of forming hydrogen bonds thereby forming self-complementary units, preferably comprising at least four hydrogen bonds in a row. Units capable of forming at least four hydrogen bonds in a row, i.e. quadruple hydrogen bonding units, as used herein are abbreviated as '4H-units'. Sijbesma et al. (U.S. Pat. No. 6,320,018B1; *Science* 278, pp 1601-1604, 1997; both incorporated herein by reference) disclose 4H-units that are based on 2-ureido-4-pyrimidones (UPy's). These 2-ureido-4-pyrimidones are derived from isocytosines.

A low molecular weight supramolecular polymer based on telechelic polycaprolactone (PCL) end-capped with 4H-units based on 6-methyl isocytosine is disclosed in Dankers et al. (*Nature Materials* 4, 5688, 2005; incorporated herein by reference). DSC-thermograms of this supramolecular material revealed the highly crystalline nature of the PCL backbone, which has a detrimental effect on elasticity and strongly limits durability of the material. Dankers et al. further characterized mechanical behaviour of supramolecular material comprising PCL with several 4H-units along the backbone (see Biomaterials 27, 5490, 2006; incorporated herein by reference). This study revealed that highly crystalline telechelic PCL with 4H-units had a Young's modulus of about 130 MPa but breaks already after about 14% elongation, whereas a much less crystalline chain extended PCL-derivative with 4H-units had a lower Young's modulus of only about 3 MPa and an elongation of break of 576% (cf. Table 1 on page 5495). Both Dankers' materials have only one melting point above 40° C. for the pristine non-annealed materials. Analogous chain-extended aliphatic polyester-derivatives with 4H-units are disclosed in WO2005/042641A1, again low Young's moduli were obtained (cf. table on page 39).

US2009/00130172, incorporated herein by reference, discloses several supramolecular biodegradable materials that comprise 4H-units mixed with bioactive molecules comprising a 4H-unit for biomedical applications, such as coatings with controlled release of drugs. Among the materials disclosed are the PCL-based materials as published by Dankers et al. (*Nature Materials* 4, 5688, 2005 and Biomaterials 27, 5490, 2006), as well as other biodegradable polyester derivatives comprising 4H-units, such as the polyadipate-based polymers chain extended with isophorone diisocyanate (IPDI) functional 4H-units of Examples 8, 12, 13, and 15. However, all these polyester-based supramolecular biodegradable materials are characterized by poor mechanical behaviour; they are either not strong enough (Young's modulus lower than 10 MPa) or not elastic enough (elongation at break of below 50%).

US2004/0087755A1, incorporated herein by reference, discloses polyurethane polymers end-capped with 4H-units based on 6-methyl isocytosine, alkyl diol chain extenders, and 4,4'-methylene bis(phenyl isocyanate) (MDI), which can be used as hot melt adhesive or TPU foam. These materials have limited tensile strengths ranging from about 2 to about 8 MPa (Table 2) or stresses at 100% elongation of between about 2 to about 3.2 MPa (Table 6). Most importantly, the aromatic MDI in these polyurethane materials hampers their possible use as biodegradable biomedical materials, since MDI is known to result in degradation products that can comprise highly toxic aniline and derivatives thereof.

US2012/116014A1, incorporated herein by reference, discloses a process for the preparation of supramolecular polymers comprising 1-50 4H-units, in which a 4H building block according to the formula 4H-$(L-F_i)_r$, wherein 4H represents a 4H-unit, L represents a divalent, trivalent, tetravalent or pentavalent linking group, $F_i$ represents a reactive group, and r is 1-4, is reacted with a prepolymer comprising a reactive group complementary to $F_i$, wherein the reaction mixture comprising said 4H building block and said prepolymer comprises less than 10 wt. % of a non-reactive organic solvent, based on the total weight of the reaction mixture. Most preferably, r is 2 and L is a divalent $C_1$-$C_{20}$ alkylene, arylene, arylalkylene or alkylarylene group. The 4H building block is preferably prepared from a precursor of an isocytosine or a melamine derivative and a diisocyanate, wherein the diisocyanate is most preferably isophorone diisocyanate (IPDI) or methylene dicyclohexane 4,4-diisocyanate (HMDI). The supramolecular polymer according to US2012/116014A1 is preferably used in coatings and adhesive compositions. Supramolecular polymers obtained according to the preferred process as disclosed in US2012/116014A1 are very stiff (high Young's modulus) and have a low elasticity such that they are practically not feasible for use in biomedical implants because of their low fatigue resistance.

WO2014/185779A1 discloses biodegradable supramolecular polymers comprising 4H-units, low molecular weight diols, diisocyanates, and biodegradable polymeric diols, specifically hydroxyl-terminated polycaprolactones and poly(ethyleneglycols), that can be used for biodegradable implants. However, the presence of the polycaprolactones makes these supramolecular polymers highly susceptible to (enzymatic) hydrolysis of the ester-bonds that constitute these polycaprolactones. Therefore, implants based on these polycaprolactone-based supramolecular polymers degrade too fast in vivo for certain biomedical applications. When implants based on these materials are used as a cardiovascular implant, a too fast degradation might lead to aneurysms after implantation, or when they are used to treat prolapses, a too fast degradation might lead to hernias. Moreover, the mechanical performance of the disclosed polycaprolactone-based supramolecular polymers is insufficient for certain biomedical applications. Young's moduli range from 30 to 80 MPa, whereas ultimate tensile strengths are all equal to or lower than 21 MPa. The presence of poly(ethylene glycol) blocks, on the other hand, in the supramolecular polymer results in too stiff polymers with low tensile strengths that are lower than 15 MPa and high water absorption which also lead to accelerated degradation.

Hence, there is a need in the art for supramolecular biodegradable materials for biomedical applications, particularly for use in biomedical implants, that have a high mechanical strength and/or high elasticity combined with durability and controlled slow bioresorption. It is therefore an object of the invitation to provide supramolecular biodegradable materials that meet these requirements and a process for the preparation of these materials.

It is another object of the present invention to provide strong, flexible and durable supramolecular biomedical polymers as well as a process for preparing such polymers, in which the supramolecular biomedical polymers have better (thermo-)mechanical properties than those of the prior art.

It is still another object of the present invention to provide durable supramolecular biomedical polymers that can be used in biomedical implants and scaffolds for tissue engineering, wherein the biomedical implants and scaffolds are sufficiently strong to be suitable for implantation in medical conditions requiring structural support, such as injuries to tissues that require surgical intervention.

Moreover, it is an object of the invention to provide a process for preparing porous structures such as biomedical implants and scaffolds for tissue engineering from the supramolecular biodegradable materials It is yet another object of the invention to provide a process for preparing porous structures from the supramolecular biodegradable materials in a biomedically acceptable way, in order to be able to use said porous structures as implantable scaffolds for regenerative medicine, wherein the implant is gradually replaced by the patient's own functional tissue.

SUMMARY OF THE INVENTION

The present inventors have found that a process for the production of supramolecular biodegradable materials wherein specific 4H-units are combined with a polymer backbone that is not bioresorbable by itself, results in supramolecular biomedical polymers that have superior mechanical characteristics, such as strength, elasticity, and durability, while surprisingly being biodegradable in a controlled way due to their unique chemical architecture comprising the 4H-units.

Accordingly, the present invention relates in a first aspect to a process for the manufacture of a supramolecular biomedical polymer having an ultimate tensile strength of at least 35 MPa, as determined by test method ASTM D 1708-96 with a crosshead speed of 20 mm/min, and in a second aspect to supramolecular biomedical polymers having an ultimate tensile strength of at least 35 MPa, as determined by test method ASTM D 1708-96 with a crosshead speed of 20 mm/min, obtainable by said process, said process comprising reacting a compound F' according to Formula (1):

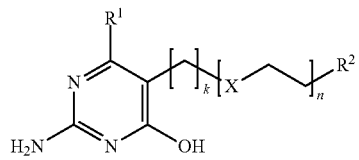

with:
- a diisocyanate compound C' according to the Formula O=C=N—R$^3$—N=C=O;
- a functionalized polymer A' according to the Formula P-(FG1)$_w$; and
- a compound B' according to the Formula FG2-R$^4$-FG2;

wherein:
- X is O or S;
- k is an integer of 1 to 20;
- n is an integer of 0 to 8;
- R$^1$ is a C$_1$-C$_{13}$ alkylene group;
- R$^2$ is a functional group selected from OH, SH and NH$_2$;
- FG1, FG2 and FG3 are functional groups independently selected from OH and NH$_2$;
- w is in the range of about 1.8 to about 2;
- functionalized polymer A' has a number average molecular weight M$_n$, as determined from its hydroxyl value, of about 250 to about 10000 Da;
- P is a polymer, with the proviso that it is neither poly(ethyleneglycol) nor polycaprolactone;
- R$^3$ is a cylic or linear C$_4$-C$_{20}$ alkylene group or a C$_4$-C$_{20}$ alkylene group comprising an ester; and
- R$^4$ is selected from the group consisting of C$_2$-C$_{44}$ alkylene, C$_6$-C$_{44}$ arylene, C$_7$-C$_{44}$ alkarylene and C$_7$-C$_{44}$ arylalkylene, wherein the alkylene groups, arylene groups, alkarylene groups and arylalkylene groups are optionally interrupted by 1-5 heteroatoms selected from the group consisting of O, N and S; and
- wherein the molar ratio of compounds A', B', C' and F' expressed as A':B':C':F' is between 1:1.5:3.5:1 and 1:2:4:1.

In a third aspect, the invention relates to a porous biomedical implant comprising the supramolecular biomedical polymer obtainable by the process as defined hereinbefore.

In a fourth aspect, the invention relates to a process for the manufacture of a porous biomedical implant having a non-woven mesh structure comprising the supramolecular biomedical polymer obtainable by the process as defined hereinbefore, said process for the manufacture of a porous biomedical implant comprising the steps of:
a) providing the supramolecular biomedical polymer obtainable by the process as defined hereinbefore;
b) dissolving the supramolecular biomedical polymer according to (a) in a solvent mixture suitable for electro-spinning;
c) electro-spinning the polymer solution according to (b) on a target; and
d) isolating the porous biomedical implant from the target as a sheet, cylinder, or complex 3D-structure.

In a fifth aspect, the invention relates to a porous biomedical implant as defined hereinbefore or obtainable by the electro-spinning process as defined hereinbefore, for use in the treatment of cardio-vascular diseases, said treatment comprising the replacement of part of an artery or vein, or part or all of a venous, pulmonary, mitral, tricuspid, or aortic heart valve in a mammalian subject with said porous biomedical implant, wherein the porous biomedical implant acts as a scaffold for the formation of new cardio-vascular tissue.

In a sixth aspect, the invention relates to a porous biomedical implant as defined hereinbefore or obtainable by the electro-spinning process as defined hereinbefore, for use in the treatment of cardio-vascular diseases, said treatment comprising the positioning of said implant at an intracardiac or intravascular site in a mammalian subject, wherein the porous biomedical implant acts as a scaffold for the formation of new cardio-vascular tissue.

In a seventh aspect, the invention relates to a porous biomedical implant as defined hereinbefore or obtainable by the electro-spinning process as defined hereinbefore, for use in the treatment of a medical condition requiring reconstruction surgery, support or augmentation, preferably prolapse, pelvic organ prolapse, compartment syndrome, constrictive pericarditis, hemopneumothorax, hemothorax, injuries to the Dura mater, and hernias, such as abdominal, diaphragmatic, hiatal, pelvic, anal, intracranial, spigelian hernias, and hernias of the nucleus pulposus of the intervertebral discs, and stress urinary incontinence, said treatment comprising surgical implantation of the porous biomedical implant at the site of a mammalian subject that needs reconstruction surgery, support or augmentation, wherein the porous biomedical implant acts as a scaffold for the formation of new tissue.

General Definitions

The 'hydroxyl value' is defined as the number of milligrams of potassium hydroxide required to neutralize the acetic acid taken up on acetylation of one gram of a chemical substance that contains free hydroxyl groups. Hydroxyl value is a measure of the content of free hydroxyl groups in a chemical substance, usually expressed in units of the mass of potassium hydroxide (KOH) in milligrams equivalent to the hydroxyl content of one gram of the chemical substance. The molecular weight of P-(FG1)$_w$, as used in the present invention, is equal to (2×56.1×1000)/(hydroxyl value).

The term 'scaffold' as used herein refers to a porous structure comprising a supramolecular biomedical polymer, used to guide the organization, growth, and differentiation of cells in the process of forming new functional tissue at the site of a tissue defect or wound, typically used in conjunction with surgical intervention.

The term 'durable' in the context of 'durable supramolecular biomedical polymer' or 'durable supramolecular biomedical material' or 'durable biomedical implant' as used herein refers to material that has a fatigue resistance high enough for its application.

The term 'obtainable by' is considered to be synonymous to 'obtained by'.

The term 'one step reaction' as used herein refers to a 'one pot reaction', wherein all reactants are present at the same time and are added substantially simultaneously, as opposed to a reaction comprising sequential reaction steps' wherein a subsequent reactant is added after (at least partial) completion of a previous reaction step, possibly in different reaction vessels.

An urea moiety as indicated in this document is to be understood as a moiety according to the formula:

—NR—C(=X)—NR— wherein X is O or S, preferably O; and wherein both moieties R are chosen independently from one another from a hydrogen atom or a linear alkyl group, preferably a hydrogen atom.

An amide moiety as indicated in this document is to be understood as a moiety according to the formula:

—NR—C(=X)— wherein X and R are as described above.

A urethane moiety as indicated in this document is to be understood as a moiety according to the formula:

—NR—C(=X)—X— wherein R is as described above and wherein both atoms X are chosen independently from one another from O or S, wherein X preferably is O.

An ester moiety as indicated in this document is to be understood as a moiety according to the formula:

—C(=X)—X— wherein both atoms X are chosen independently from one another from O or S, wherein X preferably is O.

A carbonate moiety as indicated in this document is to be understood as a moiety according to the formula:

—X—C(=X)—X— wherein all three atoms X are chosen independently from one another from O or S, wherein X preferably is O.

An amine moiety as indicated in this document is to be understood as a moiety according to the formula:

—NR$_2$— wherein R is as described above.

An ether moiety as indicated in this document is to be understood as a moiety according to the formula:

—X— wherein X is as described above.

An isocyanate group is to be understood as a —N=C=X group, wherein X is as described above.

(Self)-complementary units capable of forming at least four hydrogen bonds form in principle non-covalent moieties with each other. When the (self)-complementary units are capable of forming four hydrogen bonds in a row, they are used in their abbreviated form '4H-unit'. However, it is within the scope of this invention that the (self)-complementary units (including the 4H-units) can form non-covalent moieties with other materials capable of forming less than four hydrogen bonds. Units capable of forming at least four hydrogen bonds can form a non-self-complementary or a self-complementary binding group. 'Non-self-complementary' means for example that a 4H-unit (I) forms a bonding moiety (I)-(II) with a unit (II), wherein (II) is a different 4H-unit. 'Self-complementary' means that two 4H-units (I) form a bonding moiety (I)-(I). It is preferred that the 4H-unit is self-complementary. The units according to compound F' of Formula (1) form, when incorporated in the supramolecular biomedical polymer according to the present invention, (self)-complementary units.

The terms 'bioresorbable', 'biodegradable' and 'biodegradation' as used in this document relate to cell-mediated degradation, enzymatic degradation and hydrolytic, oxidative degradation of the supramolecular biomedical polymer and/or the porous biomedical implant comprising the supramolecular biomedical polymer. The term 'biodegradable' may also relate to elimination of the supramolecular biomedical polymer and/or the porous biomedical implant comprising the supramolecular biomedical polymer from living tissue.

The term 'tissue' as used in this document refers to a solid living tissue which is part of a living mammalian individual, such as a human being. The tissue may be a hard tissue or a soft tissue including ligaments, tendons, fibrous tissue, fascia, fat, muscles, nerves, and cardiovascular tissue.

The term 'room temperature' as used in this document has its normal meaning, i.e. it indicates a temperature in the range of about 20° C. to about 25° C.

Molecular weights such as $M_n$ are expressed in Dalton (Da).

DETAILED DESCRIPTION OF THE INVENTION

Process for Preparing Supramolecular Biomedical Polymers

In a first aspect, the present invention relates to a process for the manufacture of a supramolecular biomedical polymer having an ultimate tensile strength of at least 35 MPa, as determined by test method ASTM D 1708-96 with a cross-head speed of 20 mm/min, said process comprising reacting a compound F' according to Formula (1):

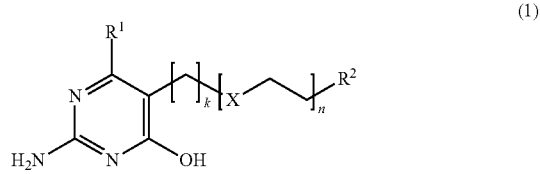

(1)

with:
a diisocyanate compound C' according to the Formula O=C=N—R$^3$—N=C=O;
a functionalized polymer A' according to the Formula P-(FG1)$_w$; and
a compound B' according to the Formula FG2-R$^4$-FG3;
wherein:
X is O or S;
k is an integer of 1 to 20;
n is an integer of 0 to 8;
R$^1$ is a C$_1$-C$_{13}$ alkylene group;
R$^2$ is a functional group selected from OH, SH and NH$_2$;
FG1, FG2 and FG3 are functional groups independently selected from OH and NH$_2$;
w is in the range of about 1.8 to about 2;
functionalized polymer A' has a number average molecular weight $M_n$, as determined from its hydroxyl value, of about 250 to about 10000 Da;
P is a polymer, with the proviso that it is neither poly (ethyleneglycol) nor polycaprolactone;
R$^3$ is a cylic or linear C$_4$-C$_{20}$ alkylene group or a C$_4$-C$_{20}$ alkylene group comprising an ester; and
R$^4$ is selected from the group consisting of C$_2$-C$_{44}$ alkylene, C$_6$-C$_{44}$ arylene, C$_7$-C$_{44}$ alkarylene and C$_7$-C$_{44}$ arylalkylene, wherein the alkylene groups, arylene groups, alkarylene groups and arylalkylene groups are optionally interrupted by 1-5 heteroatoms selected from the group consisting of O, N and S; and
wherein the molar ratio of compounds A', B', C' and F' expressed as A':B':C':F' is between 1:1.5:3.5:1 and 1:2:4:1.

The process results in supramolecular biomedical polymers having a high (ultimate) tensile strength, high elasticity, high durability, which are very suitable for biomedical applications.

The process for the manufacture of a supramolecular biomedical polymer preferably is a process for the manufacture of a supramolecular biomedical polymer having a Young's modulus ($E_{mod}$) of at least 40 MPa, more preferably at least 50 MPa, even more preferably of at least 90 MPa, as determined by test method ASTM D 1708-96 with a crosshead speed of 20 mm/min, preferably measured between 0.25 and 2.50% elongation. Preferably, the Young's modulus ($E_{mod}$) is lower than 180 MPa, more preferably lower than 160 MPa, most preferably lower than 140 MPa, as determined by test method ASTM D 1708-96 with a crosshead speed of 20 mm/min, preferably measured between 0.25 and 2.50% elongation. In a very preferred embodiment, the Young's modulus ($E_{mod}$) is between 40 and 160 MPa, as determined by test method ASTM D 1708-96 with a crosshead speed of 20 mm/min, preferably measured between 0.25 and 2.50% elongation.

The process for the manufacture of a supramolecular biomedical polymer preferably is a process for the manufacture of a supramolecular biomedical polymer having a modulus at 100% elongation of at least 7 MPa, more preferably at least 12 MPa, most preferably at least 15 MPa, as determined by test method ASTM D 1708-96 with a crosshead speed of 20 mm/min.

The process for the manufacture of a supramolecular biomedical polymer preferably is a process for the manufacture of a supramolecular biomedical polymer having an ultimate tensile strength of at least 40 MPa, more preferably of at least 45 MPa, as determined by test method ASTM D 1708-96 with a crosshead speed of 20 mm/min.

The process for the manufacture of a supramolecular biomedical polymer preferably is a process for the manufacture of a supramolecular biomedical polymer having an elongation at break of at least 350%, more preferably of at least 400%, and most preferably of at least 500%, as determined by test method ASTM D 1708-96 with a crosshead speed of 20 mm/min.

The process for the manufacture of a supramolecular biomedical polymer preferably is a process for the manufacture of a supramolecular biomedical polymer having a fatigue resistance of at least 3 million cycles before failure, preferably at least 6 million cycles, and most preferably at least 12 million cycles, as determined on a strip of polymer of 5×25 mm with a thickness in between 0.2 and 1 mm, using a uniaxial tensile tester with an elongation of 10% at a sample rate of 2 Hz or 10 Hz, preferably 10 Hz, whereby fatigue failure is defined at the cycle in which the stress response is below 10% of the stress response at the first cycle.

The process for the manufacture of a supramolecular biomedical polymer preferably is a process for the manufacture of a supramolecular biomedical polymer having at least two thermal transitions selected from glass transitions and melting points at a temperature between about 50° C. and about 125° C., and no thermal transition in between 0° C. and 45° C., preferably no thermal transition in between 0° C. and 40° C., and preferably no thermal transition above 125° C., as determined with differential scanning calorimetry (DSC) at a heating rate of 20° C./min. In a very preferred embodiment, the process for the manufacture of a supramolecular biomedical polymer is a process for the manufacture of a supramolecular biomedical polymer having at least two thermal transitions selected from glass transitions and melting points at a temperature between about 50° C. and about 125° C., and no thermal transitions in between 0° C. and 45° C., as determined with differential scanning calorimetry (DSC) at a heating rate of 20° C./min.

The process for the manufacture of a supramolecular biomedical polymer preferably is a process for the manufacture of a supramolecular biomedical polymer having a deformation-quotient defined by the ultimate tensile strength divided by the modulus at 100% elongation of at least 2.0, more preferably of at least 2.5, and most preferably of at least 3.5, whereby the ultimate tensile strength and the modulus at 100% elongation are according to test method ASTM D 1708-96 with a crosshead speed of 20 mm/min.

The process for the manufacture of a supramolecular biomedical polymer preferably is a process for the manufacture of a supramolecular biomedical polymer having at least one of the preferred (thermo-) mechanical properties chosen from the group consisting of ultimate tensile strength, Young's modulus, modulus at 100% elongation, elongation at break, thermal transitions, deformation-quotient and fatigue resistance as described hereinbefore.

In a very preferred embodiment, the process for the manufacture of a supramolecular biomedical polymer is a process for the manufacture of a supramolecular biomedical polymer having an ultimate tensile strength of at least 35 MPa, more preferably of at least 40 MPa, most preferably of at least 45 MPa, as determined by test method ASTM D 1708-96 with a crosshead speed of 20 mm/min and a fatigue resistance of at least 3 million cycles before failure, preferably at least 6 million cycles, and most preferably at least 12 million cycles, as determined on a strip of polymer of 5×25 mm with a thickness in between 0.2 and 1 mm, using a uniaxial tensile tester with an elongation of 10% at a sample rate of 2 Hz or 10 Hz, preferably 10 Hz, whereby fatigue failure is defined at the cycle in which the stress response is below 10% of the stress response at the first cycle.

In a very preferred embodiment, the process for the manufacture of a supramolecular biomedical polymer is a process for the manufacture of a supramolecular biomedical polymer having all of the preferred (thermo-) mechanical properties chosen from the group consisting of ultimate tensile strength, Young's modulus, modulus at 100% elongation, elongation at break, thermal transitions, deformation-quotient and fatigue resistance as described hereinbefore.

In a very preferred embodiment, the process for the manufacture of a supramolecular biomedical polymer is a process for the manufacture of a supramolecular biomedical polymer having at least one of the following properties (i) to (vi):
  i) a Young's modulus of between 40 and 160 MPa, as determined by test method ASTM D 1708-96 with a crosshead speed of 20 mm/min;
  ii) a modulus at 100% elongation of at least 7 MPa, as determined by test method ASTM D 1708-96 with a crosshead speed of 20 mm/min;
  iii) an ultimate tensile strength of at least 40 MPa, as determined by test method ASTM D 1708-96 with a crosshead speed of 20 mm/min;
  iv) an elongation at break of at least 350%, as determined by test method ASTM D 1708-96 with a crosshead speed of 20 mm/min;
  v) a fatigue resistance of at least 3 million cycles before failure, as determined on a strip of polymer of 5×25 mm with a thickness in between 0.2 and 1 mm, using a uniaxial tensile tester with an elongation of 10% at a sample rate of 10 Hz, whereby fatigue failure is defined at the cycle in which the stress response is below 10% of the stress response at the first cycle; and vi) at least two thermal transitions selected from glass transitions and melting points at a temperature between 50 and 125° C. and no thermal transition in between 0 and 45° C., as determined with differential scanning calorimetry at a heating rate of 20° C./min.

In a most preferred embodiment, the process for the manufacture of a supramolecular biomedical polymer is a process for the manufacture of a supramolecular biomedical polymer having all of the properties (i) to (vi).

Preferably, in this process, functionalized polymer A', compound B', diisocyanate compound C' and compound F' according to Formula (1) are reacted in a one step reaction. This requires adding A', B', C' and F' to a reaction vessel more or less simultaneously.

It is preferred that the ratio of the molar amounts of components A', B', C' and F', expressed as A':B':C':F', is between 1:1.5:3.5:1 to 1:2:3.97:1. In another preferred embodiment, the molar amount of C' is equal to about 0.8 to about 1.2 times the total molar amount of functionalized polymer A' plus compound B' plus compound F' according to Formula (1).

In another embodiment, the process comprises reacting the functionalized polymer A', compound B', diisocyanate compound C' and compound F' according to Formula (1) in distinct reaction steps.

Accordingly, an embodiment relates to a sequential reaction process for preparing the supramolecular biomedical polymer:

a) wherein a compound F' according to Formula (1) is reacted in a first step with a diisocyanate compound C' according to the Formula O=C=N—$R^3$—N=C=O and a functionalized polymer A' according to the Formula P-$(FG1)_w$ to form a prepolymer P1 comprising compound F' according to Formula (1); and b) wherein in a second step the supramolecular biomedical polymer is formed by the reaction of prepolymer P1 comprising compound F' according to Formula (1) from step (a) with compound B' according to the Formula FG2-$R^4$-FG3 and optionally diisocyanate compound C'.

In this sequential reaction, the functionalized polymer A', compound F' according to Formula (1) and diisocyanate compound C' are preferably reacted in step (a) in a molar ratio expressed as A':F':C' of between 1:1:1 and 1:1:4, more preferably in a molar ratio of between 1:1:3.5 and 1:1:4, most preferably 1:1:4, and in step (b) in a molar ratio expressed as P1:B' of between 1:1.5 and 1:2, with the optionally addition of further diisocyanate compound C' in step (b) to equal the molar amount of diisocyanate compound C' with the molar amounts of functionalized polymer A' plus compound B' plus compound F' according to Formula (1).

In another embodiment, a sequential reaction process for preparing the supramolecular biomedical polymer is provided:

a) wherein in a first step in a first reaction vessel functionalized polymer A' and diisocyanate compound C' are reacted to form a prepolymer P1 and in a second reaction vessel compound F' according to Formula (1) and diisocyanate compound C' are reacted to form a functionalised compound F'; and b) wherein in a second step prepolymer P1 and functionalised compound F' are combined and reacted with 1.5-2 molar equivalents of compound B' and additional 0-1 molar equivalents of diisocyanate compound C', preferably 0 additional molar equivalents of diisocyanate compound C'.

In this sequential reaction, functionalized polymer A' and diisocyanate compound C' on the one hand and compound F' according to Formula (1) and diisocyanate compound C' on the other hand are preferably reacted in step (a) in a molar ratio of 1:2 of functionalized polymer A', respectively compound F' according to Formula (1), to diisocyanate compound C'. Prepolymer P1 and functionalised compound F' according to Formula (1) are preferably reacted in step (b) with 1.5-2 molar equivalents of compound B', and 0-4 molar equivalents of diisocyanate compound C'.

Alternatively, the supramolecular biomedical polymer may be obtained by adding functionalized polymer A', compound B', diisocyanate compound C' and compound F' according to Formula (1) in any order in one or multiple steps.

Without wishing to be bound by theory, it is believed that the major course of the reactions is as schematically shown in Scheme 1, wherein FG1, FG2, FG3 and $R^2$ represent OH and wherein w=2.

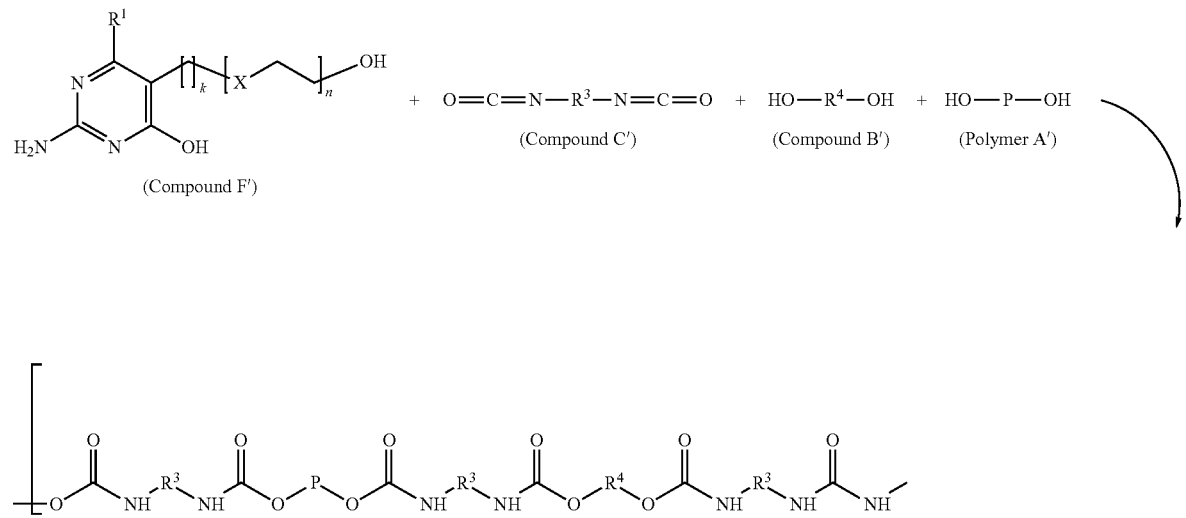

-continued

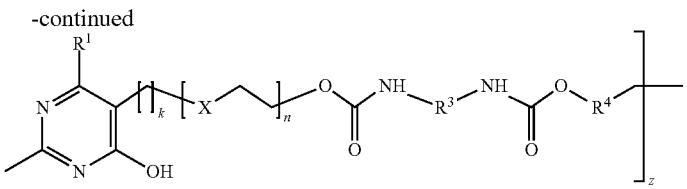

wherein z is such that the number average molecular weight $M_n$ of the supramolecular biomedical polymer is about 3000 to about 150000 Da as determined with size-exclusion chromatography in DMF comprising 10 mM LiBr at 50° C. using PEO/PEG-standards. It is preferred that z is in the range of 6 to 20, more preferably 10 to 18.

Compound F' According to Formula (1)

The group $R^1$ in compound F' according to formula (1) is a $C_1$-$C_{13}$ alkylene group. The $C_1$-$C_{13}$ alkylene group can be cyclic, branched, or linear. More preferably, $R^1$ is selected from the group consisting of methyl, ethyl, propyl, isopropyl, n-butyl, t-butyl, n-hexyl, cyclohexyl, 3-ethylpentyl and tredecyl. Most preferably $R^1$ is methyl.

In compound F' according to formula (1), k is an integer from 1 to 20, preferably 2, 4 or 11, most preferably 2, and n is an integer from 0 to 8, preferably 0 or 1, most preferably 0. X can be oxygen (O) or sulphur (S), preferably oxygen.

The functional group that is present as $R^2$ in compound F' according to formula (1) is an amino ($NH_2$), thiol (SH), or hydroxyl group (OH), preferably a primary amino group or hydroxyl group, most preferably a hydroxyl group.

In very preferred embodiments, in the compound F' according to formula (1), $R^1$ is methyl and:
a) k is 2, n is 0, and $R^2$ is OH;
b) k is 2, n is 1, $R^2$ is OH and X is O;
c) k is 4 to 11, n is 0, $R^2$ is OH; or
d) k is 4 to 11, n is 0, $R^2$ is $NH_2$.

Diisocyanate Compound C'

The diisocyanate compound C' has the Formula $O=C=N-R^3-N=C=O$, wherein $R^3$ is a cyclic or linear $C_4$-$C_{20}$ alkylene group or a $C_4$-$C_{20}$ alkylene group comprising an ester. More preferably, $R^3$ is a linear $C_4$-$C_{20}$ alkylene group. Even more preferably, the diisocyanate compound C' is selected from the group consisting of 1,4-diisocyanatobutane (BDI), 1,6-diisocyanatohexane (HDI) and 1,12-diisocyanatododecane. Most preferably, the diisocyanate compound C' is 1,6-diisocyanatohexane.

In another embodiment of this invention, the diisocyanate compound C' is lysine alkyl ester diisocyanate, more preferably L-lysine ethyl ester diisocyanate.

Functionalized Polymer A'

The functionalized polymer A' has the formula P-(FG1)$_w$ wherein w is in the range of about 1.8 to about 2. FG1 is a functional group selected from OH and $NH_2$. The functionalized polymer A' is either functionalized with OH or with $NH_2$.

In a preferred embodiment, w is in the range of about 1.9 to about 2, more preferably in the range of about 1.95 to about 2. In case functionalized polymer A' is exactly bifunctional, i.e. if w=2, functionalized polymer A' is represented by FG1-P-FG1.

In a very preferred embodiment, the polymer P in functionalized polymer A' having the formula P-(FG1)$_w$ is end-group functionalized with FG1.

Functionalized polymer A' has a number average molecular weight $M_n$ as determined from its hydroxyl value of about 250 to about 10000 Da, more preferably about 500 to about 4000 Da, even more preferably about 900 to 2100 Da, such as about 1000 to about 2000 Da, still more preferably about 950 to about 1500, and most preferably about 900 to about 1200 Da, such as about 1000 to about 1200 Da.

The polymer P in functionalized polymer A' can be selected from all kinds of polymer backbones, with the proviso that it neither comprises polycaprolactone nor poly(ethyleneglycol). Most preferably, the polymer A' is a linear polymer P functionalized with hydroxyl end-groups, which implies that FG1 represents OH.

Preferably, functionalized polymer A' is a hydrophobic polymer that is neither FG1-functionalized polycaprolactone nor poly(ethyleneglycol). Hydrophobic functionalized polymers A' are preferred in order to prevent that the biodegradation of the supramolecular biomedical polymer is too fast in an aqueous environment such as the aqueous environment that constitutes living tissue. According to this invention, hydrophobic polymers have a solubility in water at 25° C. that is lower than 10 g/L, more preferably lower than 1 g/L, most preferably lower than 0.1 g/L. Alternatively, hydrophobic polymers have a water contact angle higher than 70°, more preferably higher than 75°, and most preferably higher than 80°, as measured at 25° C. using a static sessile drop method in which method a contact angle goniometer is used to determine the contact angle, wherein the contact angle is defined as the angle between the surface of the solid polymer and the tangent of the water droplet's ovate shape at the edge of the droplet.

The functionalized polymer A' is preferably a FG1-functionalized polymer P-(FG1)$_w$ wherein P is selected from the group consisting of polyethers, polyesters, polyorthoesters, polyamides, polypeptides, polyacrylates, polymethacrylates, polycarbonates, polybutadienes, hydrogenated polybutadienes, and co-polymers of such polymers. More preferably, the functionalized polymer A' is a FG1-functionalized polymer P-(FG1)$_w$, wherein P is selected from the group consisting of polyethers, polyamides, polycarbonates, polybutadienes, hydrogenated polybutadienes, polypeptides and co-polymers of such polymers. Even more preferably, the functionalized polymer A' is a FG1-functionalized polymer P-(FG1)$_w$, wherein P is selected from the group consisting of polycarbonates, polybutadienes, hydrogenated polybutadienes and copolymers of such polymers.

In one specific embodiment of this invention, the functionalized polymer A' is a FG1-functionalized polymer P-(FG1)$_w$, wherein P is selected from the group consisting of polycarbonates, polyethers, and copolymers of such polymers. Most preferably, the functionalized polymer A' is a FG1-functionalized polycarbonate.

FG1-functionalized polycarbonates are preferably selected from hydroxy terminated polycarbonates and hydroxy terminated copolycarbonates based on alkyldiol polycarbonate and hydroxy terminated polycarbonates and hydroxy terminated copolycarbonates made by ring opening polymerization of trimethylenecarbonate, 1,3-dioxepane-2-one, 1,3-dioxanone-2-one, and 1,3,8,10-tetraoxacyclotetradecane-2,9-dione. More preferably, FG1-functionalized polycarbonates are selected from hydroxy terminated alkyldiol polycarbonate, most preferably hydroxy terminated poly(1,6-hexanediol) carbonate.

In another specific embodiment of this invention, the functionalized polymer A' is selected from the group consisting of polyethers with the proviso that it is not FG1-functionalized poly(ethyleneglycol).

FG1-functionalized polyethers are preferably selected from end group FG1-functionalized polypropylene glycols, poly(ethylene-co-propylene) glycols (random or block), poly(ethylene-block-propylene-block-ethylene) glycols (also known as Pluronics®), poly(tetramethylene ether)glycols (i.e. poly-tetrahydrofurans) and poly(ethylene-co-tetramethylene ether)glycols, and their copolyethers. More preferably, the FG1-functionalized polyether is an end group FG1-functionalized poly(tetramethylene ether)glycol.

FG1-functionalized (Hydrogenated) polybutadienes are preferably end group functionalized and selected from FG1-functionalized low cis, high cis and high vinyl polybutadienes. Preferably, they are selected from the group consisting of FG1-functionalized polybutylene with high 1,2-vinyl structure, FG1-functionalized hydrogenated polybutadiene or FG1-functionalized hydrogenated 1,2-polybutadiene.

It was surprisingly found that when using a functionalized polymer A' different from FG1-functionalized polycaprolactone or poly(ethyleneglycol), such as FG1-functionalized polycarbonates, FG1-functionalized polybutadienes, FG1-functionalized hydrogenated polybutadienes, and FG1-functionalized poly(tetramethylene ether)glycols, beneficial material performances were obtained for the supramolecular biomedical polymers in relation to their use in porous biomedical implants. More specifically, in relation to their elastomeric behaviour, durability, and resistance towards gamma and electron-beam sterilization. Additionally, notwithstanding the relatively non-degradable nature of these functionalized polymers A', due to their resistance to hydrolysis by lacking ester bonds in their polymer backbone, it was found that the corresponding supramolecular biomedical polymers comprising the functionalized polymer A' backbones actually do degrade in vivo after implantation. Without wishing to be bound by theory, this in vivo degradation is thought to originate in biodegradation of the compounds F' according to Formula (1) that are comprised in the supramolecular biomedical polymer.

Compound B'

The compound B' has the Formula FG2-$R^4$-FG3, wherein $R^4$ is selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups are optionally interrupted by 1-5 heteroatoms selected from the group consisting of O, N and S. FG2 and FG3 are functional groups independently selected from OH and $NH_2$.

Preferably, $R^4$ is a $C_2$-$C_{20}$ alkylene group, which is optionally interrupted with one or more, preferably 1-5, oxygen or nitrogen atoms. The alkylene groups may be linear or cyclic.

More preferably, $R^4$ is a linear $C_2$-$C_{20}$ alkylene group, even more preferably $R^4$ is selected from the group consisting of butylene, hexylene, octylene, decylene, and dodecylene. Most preferably, $R^4$ is hexylene.

Preferably, FG2 and FG3 are the same, more preferably FG2 and FG3 are both OH.

The compound B' preferably has a molecular weight of about 130 to about 400 Da, more preferably a molecular weight of about 130 to about 190 Da.

Preferably, the compound B' is a linear $C_2$-$C_{12}$ alkyl α,ω-diol, wherein the alkylene group is optionally interrupted with one or more, preferably 1-5, oxygen atoms. Even more preferably the compound B' is selected from 1,4-butanediol, 1,12-dodecyldiol and 1,6-hexanediol. Most preferably, the compound B' is 1,6-hexanediol.

In another embodiment of this invention, FG2 is OH and FG3 is $NH_2$ and $R^4$ is a linear $C_2$-$C_{20}$ alkylene group, even more preferably $R^4$ is selected from the group consisting of butylene, hexylene, octylene, decylene, and dodecylene, most preferably hexylene.

The Process

The process for the preparation of the supramolecular biomedical polymer according to this invention can be performed by any method known in the art, for example in solution or in the bulk using reactive extrusion. The process is, irrespective of whether it is performed as a one step process or as a sequential process comprising two or more reaction steps, preferably performed at a temperature between about 10° C. and about 140° C., more preferably between about 20° C. and about 120° C., and most preferably between about 40° C. and about 90° C.

The process for the preparation of the supramolecular biomedical polymer may be performed in the presence of a catalyst. Examples of suitable catalysts promoting the reaction between isocyanates and hydroxyl groups are known in the art. Preferred catalysts include tertiary amines and catalysts comprising a metal. Preferred tertiary amines are 1,4-diazabicyclo[2.2.2]octane (DABCO) and 1,8-diazabicyclo[5.4.0]undec-7-ene (DBU). Preferred catalysts comprising a metal are tin(IV) compounds and zirconium(IV) compounds, preferably selected from the group consisting of tin(II)octanoate, dibutyltin(IV)laurate and zirconium(IV)acetoacetate. Most preferably, the catalyst is tin(II)octanoate or zirconium(IV)acetoacetate. The amount of catalyst is generally below about 1% by weight, preferably below about 0.2% by weight and most preferably in between 0.05 and 0.15% by weight, based on the total amount of reactants A', B', C' and F'.

In a preferred embodiment of this invention, the process is performed in the presence of a non-reactive polar organic solvent, wherein it is preferred that the amount of the non-reactive polar organic solvent is at least about 20 weight %, more preferably at least about 40 weight %, even more preferably at least about 50 weight %, and most preferably at least about 70 weight %, based on the total weight of the reaction mixture A', B', C' and F' that is formed in either a one step process or in a sequential process comprising two or more reaction steps. It is also preferred that the reaction mixture does not comprise any inorganic solvents such as water. Non-reactive solvents are preferably selected from non-protic polar organic solvents, preferably tetrahydrofuran, dioxane, N-methylpyrrolidone, dimethylformamide, dimethylacetamide, dimethyl sulfoxide, propylene carbonate, ethylene carbonate and 2-methoxy-ethyl-acetate. Most preferably, the non-reactive polar organic solvent is dimethyl sulfoxide or propylene carbonate.

The supramolecular biomedical polymer can be isolated as such, i.e. as polymer in solvent, or can be isolated as a powder after precipitation in a non-solvent, chopped into pellets, spun into fibers, extruded into films, directly dissolved in a medium of choice, or transformed or formulated into whatever form that is desired.

In a very preferred embodiment, the process for the manufacture of a supramolecular biomedical polymer comprises reacting a compound F' according to Formula (1):

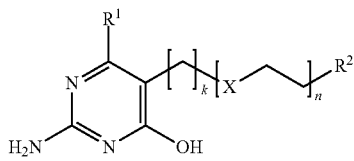
(1)

with:
a diisocyanate compound C' according to the Formula O=C=N—$R^3$—N=C=O;
a functionalized polymer A' according to the Formula P-(FG1)$_w$; and
a compound B' according to the Formula FG2-$R^4$-FG3;
wherein:
X is O or S;
k is an integer of 1 to 20;
n is an integer of 0 to 8;
$R^1$ is a $C_1$-$C_{13}$ alkylene group;
$R^2$ is a functional group selected from OH, SH, and $NH_2$;
FG1, FG2, and FG3 are functional groups independently selected from OH and $NH_2$;
w is in the range of about 1.8 to about 2;
functionalized polymer A' has a number average molecular weight $M_n$, as determined from its hydroxyl value, of about 1000 to about 2000 Da,
P is a polymer, with the proviso that it is neither poly (ethyleneglycol) nor polycaprolactone;
$R^3$ is a linear $C_4$-$C_{20}$ alkylene group;
$R^4$ is a linear $C_2$-$C_{20}$ alkylene group; and
wherein the molar ratio of compounds A', B', C' and F' expressed as A':B':C':F' is between 1:1.5:3.5:1 and 1:2:4:1.

Supramolecular Biomedical Polymer

In a second aspect, the invention relates to a supramolecular biomedical polymer having an ultimate tensile strength of at least 35 MPa, as determined by test method ASTM D 1708-96 with a crosshead speed of 20 mm/min, obtainable by the process as defined hereinbefore. This second aspect can also be worded as a supramolecular biomedical polymer having an ultimate tensile strength of at least 35 MPa, as determined by test method ASTM D 1708-96 with a crosshead speed of 20 mm/min, obtained by the process as defined hereinbefore.

The supramolecular biomedical polymer obtainable by the process as defined hereinbefore preferably has a number average molecular weight $M_n$ of about 3000 to about 150000 Da, more preferably about 4000 to about 60000 Da, even more preferably about 8000 to about 40000 Da, yet even more preferably about 10000 to about 30000 Da, and most preferably about 10000 to about 20000 Da, as determined with size-exclusion chromatography in DMF comprising 10 mM LiBr at 50° C. using PEG/PEO-standards. As is known to the skilled person, the number average molecular weight $M_n$ of the supramolecular biomedical polymer can be adjusted by changing the molar amount of the diisocyanate compound C' with respect to the molar amounts of the further reactants.

The supramolecular biomedical polymer obtainable by the process as defined hereinbefore may be a random polymer in which the structural units resulting from the reactants A', B', C' and F' occur in random sequences. The supramolecular biomedical polymer may also be a segmented polymer in which regular sequences of structural units resulting from the reactants A', B', C' and F' can be found.

In a preferred embodiment of this invention, the supramolecular biomedical polymer obtainable by the process as defined hereinbefore absorbs less than about 2% by weight of water, based on the total weight of the supramolecular biomedical polymer, when a film layer of 0.1-0.4 mm thick is soaked into an excess of demineralized water at 37° C. for 24 hours. Such a film layer can be created by dissolving the supramolecular biomedical polymer in a volatile solvent, casting a layer of the solution onto a surface and allowing the volatile solvent to evaporate.

For application in biomedical implants such as prosthetic meshes and heart valves, the (thermo-)mechanical properties of the supramolecular biomedical polymer are very important.

Without wishing to be bound by theory, it is hypothesized that the lower levels of the Young's modulus and modulus at 100% defined infra for the supramolecular biomedical polymer are needed to warrant enough strength and elasticity in a biomedical implant comprising the supramolecular biomedical polymer for its biomedical application, whereas an upper limit in the Young's modulus is needed to prevent said biomedical implant from being too stiff, or even brittle, which would lead to a low durability or rupture at the fastening locations of the porous biomedical implant to tissue, for example rupture after stitching. Moreover, minimum values for the ultimate tensile strength and elongation at break, and prolonged fatigue behaviour, are needed for good durability of the biomedical implant and its desired long lasting performance before degradation while implanted in the body. Additionally, the deformation behaviour of the porous biomedical implant reflects an elastic behaviour that is compliant with the tissue at the site of the implantation. In this invention this property is reflected in the value obtained from the ultimate tensile strength divided by the modulus at 100%.

The supramolecular biomedical polymer should certainly not displays a thermal transition around room temperature or body temperature, since this would alter the implants' mechanical properties during handling or while implanted in the body, whereas the presence of thermal transitions at higher temperature reflect the presence of ordered domains in the polymer which contribute to the mechanical strength of the polymer.

The limiting values for the mechanical properties of the supramolecular biomedical polymer according to this invention are based on the values obtained from native tissue, such as cardio-vascular tissue and abdominal tissue, which values are also given in the background of this invention, and on the decrease in strength when going from a solid material to a porous structure such as the non-woven mesh structure of the preferred porous biomedical implant comprising the supramolecular biomedical polymer. The native tissue values are multiplied with a factor of about 10-20 to obtain the limiting values for the supramolecular biomedical polymer. This multiplication is performed to counterbalance the effect of porosity of the non-woven mesh structure of the porous biomedical implant comprising the supramolecular biomedical polymer on the mechanical properties and to build in a safety margin to prevent failure of the medical treatment.

Without wishing to be bound by theory, the decrease in strength of a porous biomedical implant as compared to that of the supramolecular biomedical polymer is depending on the amount of porosity and the specific topology of the porous structure, which translate in decrease of strength for the non-woven mesh structure equal to 0.07-0.10 times that of the original strength of the supramolecular biomedical polymer.

The supramolecular biomedical polymer obtainable by the process as defined hereinbefore has a high (ultimate) tensile strength, high elasticity, high durability, and is very suitable for biomedical applications.

The supramolecular biomedical polymer obtainable by the process as defined hereinbefore preferably has a Young's modulus ($E_{mod}$) of at least 40 MPa, preferably at least 50 MPa, even more preferably of at least 90 MPa, as determined by test method ASTM D 1708-96 with a crosshead speed of 20 mm/min, preferably measured between 0.25 and 2.50% elongation. Preferably, the Young's modulus ($E_{mod}$) is lower than 180 MPa, more preferably lower than 160 MPa, most preferably lower than 140 MPa, as determined by test method ASTM D 1708-96 with a crosshead speed of 20 mm/min, preferably measured between 0.25 and 2.50% elongation. In a very preferred embodiment, the Young's modulus ($E_{mod}$) is between 40 and 160 MPa, as determined by test method ASTM D 1708-96 with a crosshead speed of 20 mm/min, preferably measured between 0.25 and 2.50% elongation.

The supramolecular biomedical polymer obtainable by the process as defined hereinbefore preferably has a modulus at 100% elongation of at least 7 MPa, more preferably at least 12 MPa, most preferably at least 15 MPa, as determined by test method ASTM D 1708-96 with a crosshead speed of 20 mm/min.

The supramolecular biomedical polymer obtainable by the process as defined hereinbefore preferably has an ultimate tensile strength of at least 40 MPa, more preferably of at least 45 MPa, as determined by test method ASTM D 1708-96 with a crosshead speed of 20 mm/min.

The supramolecular biomedical polymer obtainable by the process as defined hereinbefore preferably has an elongation at break of at least 350%, more preferably of at least 400%, and most preferably of at least 500%, as determined by test method ASTM D 1708-96 with a crosshead speed of 20 mm/min.

The supramolecular biomedical polymer obtainable by the process as defined hereinbefore preferably has a fatigue resistance of at least 3 million cycles before failure, preferably at least 6 million cycles, and most preferably at least 12 million cycles, as determined on a strip of polymer of 5×25 mm with a thickness in between 0.2 and 1 mm, using a uniaxial tensile tester with an elongation of 10% at a sample rate of 2 Hz or 10 Hz, preferably 10 Hz, whereby fatigue failure is defined at the cycle in which the stress response is below 10% of the stress response at the first cycle.

The supramolecular biomedical polymer obtainable by the process as defined hereinbefore preferably has at least two thermal transitions selected from glass transitions and melting points at a temperature between about 50° C. and about 125° C., and no thermal transition in between 0° C. and 45° C., preferably no thermal transition in between 0° C. and 40° C., and preferably no thermal transition above 125° C., as determined with differential scanning calorimetry (DSC) at a heating rate of 20° C./min. In a very preferred embodiment, the supramolecular biomedical polymer obtainable by the process as defined hereinbefore has at least two thermal transitions selected from glass transitions and melting points at a temperature between about 50° C. and about 125° C., and no thermal transitions in between 0° C. and 45° C., as determined with differential scanning calorimetry (DSC) at a heating rate of 20° C./min.

The supramolecular biomedical polymer obtainable by the process as defined hereinbefore preferably has a deformation-quotient defined by the ultimate tensile strength divided by the modulus at 100% elongation of at least 2.0, more preferably of at least 2.5, and most preferably of at least 3.5, whereby the ultimate tensile strength and the modulus at 100% elongation are according to test method ASTM D 1708-96 with a crosshead speed of 20 mm/min.

In a preferred embodiment, the supramolecular biomedical polymer obtainable by the process as defined hereinbefore has at least one of the preferred (thermo-) mechanical properties chosen from the group consisting of ultimate tensile strength, Young's modulus, modulus at 100% elongation, elongation at break, thermal transitions, deformation-quotient and fatigue resistance as described hereinbefore.

In a very preferred embodiment, the supramolecular biomedical polymer obtainable by the process as defined hereinbefore has an ultimate tensile strength of at least 35 MPa, more preferably of at least 40 MPa, most preferably of at least 45 MPa, as determined by test method ASTM D 1708-96 with a crosshead speed of 20 mm/min and a fatigue resistance of at least 3 million cycles before failure, preferably at least 6 million cycles, and most preferably at least 12 million cycles, as determined on a strip of polymer of 5×25 mm with a thickness in between 0.2 and 1 mm, using a uniaxial tensile tester with an elongation of 10% at a sample rate of 2 Hz or 10 Hz, preferably 10 Hz, whereby fatigue failure is defined at the cycle in which the stress response is below 10% of the stress response at the first cycle.

In a very preferred embodiment, the supramolecular biomedical polymer obtainable by the process as defined hereinbefore has all of the preferred (thermo-) mechanical properties chosen from the group consisting of ultimate tensile strength, Young's modulus, modulus at 100% elongation, elongation at break, thermal transitions, deformation-quotient and fatigue resistance as described hereinbefore.

In a very preferred embodiment, the supramolecular biomedical polymer obtainable by the process as defined hereinbefore has at least one of the following properties (i) to (vi):
i) a Young's modulus of between 40 and 160 MPa, as determined by test method ASTM D 1708-96 with a crosshead speed of 20 mm/min;
ii) a modulus at 100% elongation of at least 7 MPa, as determined by test method ASTM D 1708-96 with a crosshead speed of 20 mm/min;
iii) an ultimate tensile strength of at least 40 MPa, as determined by test method ASTM D 1708-96 with a crosshead speed of 20 mm/min;
iv) an elongation at break of at least 350%, as determined by test method ASTM D 1708-96 with a crosshead speed of 20 mm/min;
v) a fatigue resistance of at least 3 million cycles before failure, as determined on a strip of polymer of 5×25 mm with a thickness in between 0.2 and 1 mm, using a uniaxial tensile tester with an elongation of 10% at a sample rate of 10 Hz, whereby fatigue failure is defined at the cycle in which the stress response is below 10% of the stress response at the first cycle; and
vi) at least two thermal transitions selected from glass transitions and melting points at a temperature between 50 and 125° C. and no thermal transition in between 0 and 45° C., as determined with differential scanning calorimetry at a heating rate of 20° C./min.

In a most preferred embodiment, the supramolecular biomedical polymer obtainable by the process as defined hereinbefore has all of the properties (i) to (vi).

Porous Biomedical Implant

Preferably, the supramolecular biomedical polymer obtainable by the process as defined hereinbefore is molten and melt-spun, extruded with fused deposition modelling, processed with 3D printing techniques such as laser sintering, or dissolved in a volatile organic solvent and electro-spun, in order to obtain a porous biomedical implant or scaffold for tissue engineering. Biomedical implants or scaffolds for tissue engineering can also be obtained by solvent casting, salt leaching and thermally induced phase separation.

Hence, in a third aspect, the invention relates to a porous biomedical implant comprising the supramolecular biomedical polymer obtainable by the process as defined hereinbefore. In a preferred embodiment, the biomedical implant has a non-woven mesh structure obtained by electro-spinning the supramolecular biomedical polymer obtainable by the process as defined hereinbefore from solution.

Hence, in a fourth aspect, the invention relates to a process for the manufacture of a porous biomedical implant having a non-woven mesh structure comprising the supramolecular biomedical polymer obtainable by the process as defined hereinbefore, said process comprising the steps of:
a) providing the supramolecular biomedical polymer obtainable by the process as defined hereinbefore;
b) dissolving the supramolecular biomedical polymer according to (a) in a solvent mixture suitable for electro-spinning;
c) electro-spinning the polymer solution according to (b) on a target; and
d) isolating the porous biomedical implant from the target as a sheet, cylinder, or complex 3D-structure.

The process of electro-spinning involves the dissolution of the supramolecular biomedical polymer into a suitable solvent, pumping said supramolecular biomedical polymer solution through a small orifice, such as a needle, after which the polymer solution is deposited on a target by means of an electromagnetic field. The target can be a collector screen, rotating mandrel, or more complex 3D shape. The drying of the polymer solution during the depositioning process results in the formation of polymer fibers, which give a non-woven mesh structure by the accumulation thereof.

Preferably, the solution of the supramolecular biomedical polymer used for electro-spinning contains 5-25 percent by weight of this supramolecular biomedical polymer, more preferably 10-20 percent by weight of this supramolecular biomedical polymer, most preferably 12-18 percent by weight of this supramolecular biomedical polymer. The solvent used for dissolving the supramolecular biomedical polymer comprises preferably at least two different solvents, most preferably at least three different solvents. The solvent composition and supramolecular biomedical polymer concentration are chosen in such a way that the supramolecular biomedical polymer is fully dissolved at the concentration used and that its viscosity is at the right range for electro-spinning, meaning that it is fluid enough to be pumped through a small orifice and viscous enough to result in a fiber-forming supramolecular biomedical polymer solution jet during the electro-spinning process.

In an embodiment, a first solvent is chosen from organic volatile solvents such as chloroform, dichloromethane, tetrahydrofuran, methyl-tetrahydrofuran, acetonitrile, acetone, butanone, dimethyl carbonate, diethyl carbonate, ethylacetate, propylacetate, and butylacetate, and a second solvent is chosen from polar protic solvents such as methanol, ethanol, propanol, butanol, formic acid, acetic acid, propionic acid, trifluoroacetic acid and hexafluoro-2-propanol. Optional third and further solvents can be any organic solvent but also water. Preferably, the electro-spinning solution does not comprise dimethylformamide or dimethylacetamide. The solvent mixtures can comprise any ratio of first solvent to second solvent.

Preferably, the solution comprises:
a) at least 50% by weight of the first solvent, more preferably at least 60% by weight, most preferably at least 70% by weight, in respect to the total weight of solvents comprising the electro-spinning solution;
b) at least 1% by weight of the second solvent, more preferably at least 7% by weight, even more preferably at least 18% by weight, and most preferably at least 22% by weight, in respect to the total weight of solvents comprising the electro-spinning solution; and
c) no third solvent, more preferably at least 0.1% by weight of third solvent, more preferably at least 1% by weight, even more preferably at least 5% by weight, and most preferably at least 10% by weight, in respect to the total weight of solvents comprising the electro-spinning solution.

Most preferably, the third solvent, if any, is a polar protic solvent that is not the second solvent.

Preferably, the fiber diameter after electro-spinning is at least 2 micrometer, more preferably at least 3 micrometer, and most preferably at least 4 micrometer, whereas the fiber diameter is smaller than 10 micrometer, more preferred smaller than 7 micrometer. The fiber diameter determines the strength of the non-woven mesh structure and mediates cell growth inside the non-woven mesh structure after implantation.

The biodegradability of the porous biomedical implant comprising the supramolecular biomedical polymer can be assessed with in vitro tests that are known in the art, such as for example ISO 10993-13. Specifically, enzymatic and oxidative degradation can be followed in time by measuring the decrease in mass or the molecular weight of the polymer, or the changes in tensile behaviour or visual appearances of the implant. Accelerated enzymatic degradation can be studied in water at 37° C. comprising lipases or esterases (10-100 U/ml), and oxidative degradation can be studied in water at 37° C. comprising 20% hydrogen peroxide and 0.1 M cobalt(II) chloride.

The porous biomedical implant comprising the supramolecular biomedical polymer is only partly and at least not completely biodegraded in situ at the place of surgical application until after a period of about 2 months, preferably until after a period of about 3 months, more preferably until after a period of about 6 months, most preferably until after a period of about 9 months, wherein the biodegradation level is the fraction after a certain period is determined by (the mass of the porous biomedical implant before implantation−the mass of the porous biomedical implant after a certain period of time)/by the mass of the porous biomedical implant before implantation×100%.

Preferably, said porous biomedical implant is biodegraded to a level of at most about 50%, more preferably at most about 25%, most preferably at most about 1% within a period of about 2 months, preferably within a period of about 3 months, more preferably within a period of about 6 months, most preferably within a period of about 9 months.

The porous biomedical implant that comprises the biomedical supramolecular polymer obtainable by the process as defined hereinbefore can have any shape, such as a planar thin sheet, a tube, a ring, a disk, a cylinder, a valve, or more complex 3D shapes that resemble the shape of the tissue that is intended to be replaced by the porous biomedical implant. Alternatively, the porous biomedical implant is a thin flexible fabric that can be attached directly to the region to be treated. For all shapes, the film thickness or wall thickness of the non-woven object is preferably between 100 to 1000 micrometer, more preferably between 200 to 800 micrometer, and most preferably between 250 to 600 micrometer.

In another preferred embodiment the porous biomedical implant as defined hereinbefore or obtainable by the electro-spinning process as defined hereinbefore comprises 1 to 3 leaflet structures.

In yet another preferred embodiment the porous biomedical implant as defined hereinbefore or obtainable by the electro-spinning process as defined hereinbefore has the form of a sheet comprising 0 to 6 arms or extensions for attachment to structures in the site of the implantation.

In an embodiment, the porous biomedical implant further comprises a support structure, such as a ring or a stent, preferably made of metal or metal alloys such as stainless steel or nitinol.

One or more therapeutic agents can be added to the supramolecular biomedical polymer. This can be done by simple mixing during processing or by any post-processing procedure, such as dip-coating. The therapeutic agent can be any biological material or chemical or pharmaceutical compound that positively affects biological activity such as cell-adhesion, tissue growth, or anti-inflammatory activity. Non-limiting examples of therapeutic agents that can be added to the supramolecular biomedical polymer are drugs, hormones, (oligo)peptides, glycosaminoglycans (GAG), RNA-based material, siRNA, miRNA, DNA-based material, cDNA, plasmids, or stem cells, precursor cells, or any useful cell line known in the art. The therapeutic agent might also be a contrast agent that is known in the art and that can be used in clinical imaging techniques such as MRI, CT-scan and X-ray fluorescence. The therapeutic agent can be modified with one or more 4H-units that are complementary to those used in the supramolecular biomedical polymer.

In one specific embodiment of this invention, the porous biomedical implant does not comprise any therapeutic agent, peptide, fibrin, stem cells, or contrast agent. Preferably, the porous biomedical implant does not comprise any animal-based materials and/or materials from human donors.

Preferably, the porous biomedical implant comprises only one type of supramolecular biomedical polymer obtainable by the process as defined hereinbefore and no other supramolecular biomedical polymers, more preferably only one type of supramolecular biomedical polymer obtainable by the process as defined hereinbefore and no other synthetic polymer at all, most preferably only one type of supramolecular biomedical polymer obtainable by the process as defined hereinbefore and not any other synthetic polymer, biopolymer, or peptide.

A porous biomedical implant means an implant having a certain porosity, wherein the porosity of the material refers to the volumetric fraction of the material that is composed of pores, such as spaces, gaps, holes, openings, with the remainder of the volume of the material being the supramolecular biomedical polymer as defined hereinbefore. High porosity favours infiltration by, and adsorption of the cells to be cultured inside the porous biomedical implant, thereby forming new tissue. The porosity of the porous biomedical implant is preferably at least 70%, more preferably at least 80%, and most preferably at least 90%, wherein the porosity is measured with gravimetry in which the porosity is calculated using the following formula: porosity=(density of polymer−density of implant)/density of polymer×100%, wherein the density of the polymer is the density of the supramolecular biomedical polymer used, and the density of the porous biomedical implant is the weight of the porous biomedical implant divided by the volume of the porous biomedical implant.

The preferred mechanical properties, such as moduli and tensile strength, of the supramolecular biomedical polymer as defined hereinbefore are deliberately chosen higher than the corresponding values for soft tissues that need for example to be replaced. However, the values of these mechanical properties corresponding to porous biomedical implants produced from the supramolecular biomedical polymer, such as for example non-woven mesh structures obtained by electro-spinning, are generally lower than those of the original supramolecular biomedical polymer, such that they are still close to the values for soft tissues.

In a preferred embodiment, the porous biomedical implant comprising the supramolecular biomedical polymer obtainable by the process as defined hereinbefore preferably also has fatigue resistance of at least 3 million cycles before failure, preferably at least 6 million cycles, and most preferably at least 12 million cycles as determined on a strip of said implant of 5×25 mm with a thickness in between 0.2 and 1 mm, using a uniaxial tensile tester with an elongation of 10% at a sample rate of 2 Hz or 10 Hz, preferably 10 Hz, and at a temperature of 23±2° C. or 37±2° C., preferably 37±2° C., whereby fatigue failure is defined at the cycle in which the stress response is below 10% of the stress response at the first cycle.

Medical Applications

The mechanical performances of the supramolecular biomedical polymers according to the invention, more specifically their ultimate tensile strength, fatigue resistance and thermal properties, are suitable for manufacturing porous biomedical articles, in particular porous medical implants that can be applied in soft-tissue applications such as muscular, epithelial, and cardio-vascular tissue applications. The supramolecular biomedical polymers can be applied as a film, as an object in a specific shape, as bulk material or in the form of porous structures. Furthermore, the porous biomedical implants comprising the supramolecular biomedical polymer obtainable by the process as defined hereinbefore can be used in a method of supporting, augmentation, and regeneration of living tissue within a mammalian subject In an embodiment of this invention, supramolecular biomedical polymers are processed into porous biomedical implants using electro-spinning, which porous biomedical implants are subsequently used as scaffolds for in situ tissue engineering, meaning that mammalian tissue is grown in said porous structure after it has been implanted in a body of a living individual mammal, such as a human being, dog, cat, or horse, thereby excluding the need for growing tissue outside the mammal's body before implantation. Preferably, the supramolecular biomedical polymer is biodegradable, resulting in degradation of the implant after it has been implanted in the body. Consequently, the implant is replaced by tissue over time, such that no surgical removal of the porous biomedical implant is needed at a later stage, thereby reducing clinical costs and distress for the patient.

In a fifth aspect, the invention relates to a porous biomedical implant as defined hereinbefore or obtainable by the electro-spinning process as defined hereinbefore, for use in the treatment of cardio-vascular diseases, said treatment comprising the replacement of part of an artery or vein, or part or all of a venous, pulmonary, mitral, tricuspid, or aortic heart valve in a mammalian subject with said porous biomedical implant, wherein the porous biomedical implant acts as a scaffold for the formation of new cardio-vascular tissue.

This fifth aspect can also be worded as a method of treatment of cardio-vascular diseases, said treatment comprising the replacement of part of an artery or vein, or part or all of a venous, pulmonary, mitral, tricuspid, or aortic heart valve in a mammalian subject with a porous biomedical implant as defined hereinbefore or obtainable by the electro-spinning process as defined hereinbefore, wherein the porous biomedical implant acts as a scaffold for the formation of new cardio-vascular tissue.

In a sixth aspect, the invention relates to a porous biomedical implant as defined hereinbefore or obtainable by the electro-spinning process as defined hereinbefore, for use in the treatment of cardio-vascular diseases, said treatment comprising the positioning of said porous biomedical implant at an intracardiac or intravascular site in a mammalian subject, wherein the porous biomedical implant acts as a scaffold for the formation of new cardio-vascular tissue.

This sixth aspect can also be worded as a method of treatment of cardio-vascular diseases, said treatment comprising the positioning of a porous biomedical implant as defined hereinbefore or obtainable by the electro-spinning process as defined hereinbefore at an intracardiac or intravascular site in a mammalian subject, wherein the porous biomedical implant acts as a scaffold for the formation of new cardio-vascular tissue.

In a preferred embodiment, the cardio-vascular diseases are chosen from the group consisting of chronic venous insufficiency, aortic valve stenosis, aortic insufficiency, pulmonary valve stenosis, pulmonary insufficiency and combinations thereof.

In another preferred embodiment the porous biomedical implant as defined hereinbefore or obtainable by the electro-spinning process as defined hereinbefore for use in the treatment of cardio-vascular diseases comprises 1 to 3 leaflet structures.

In a seventh aspect, the invention relates to a porous biomedical implant as defined hereinbefore or obtainable by the electro-spinning process as defined hereinbefore, for use in the treatment of a medical condition requiring reconstruction surgery, support or augmentation, preferably prolapse, pelvic organ prolapse, compartment syndrome, constrictive pericarditis, hemopneumothorax, hemothorax, injuries to the Dura mater, and hernias, such as abdominal, diaphragmatic, hiatal, pelvic, anal, intracranial, spigelian hernias, and hernias of the nucleus pulposus of the intervertebral discs, and stress urinary incontinence, said treatment comprising surgical implantation of the porous biomedical implant at the site of a mammalian subject that needs reconstruction surgery, support or augmentation, wherein the porous biomedical implant acts as a scaffold for the formation of new tissue.

This seventh aspect can also be worded as a method of treatment of a medical condition requiring reconstruction surgery, support or augmentation, preferably prolapse, pelvic organ prolapse, compartment syndrome, constrictive pericarditis, hemopneumothorax, hemothorax, injuries to the Dura mater, and hernias, such as abdominal, diaphragmatic, hiatal, pelvic, anal, intracranial, spigelian hernias, and hernias of the nucleus pulposus of the intervertebral discs, and stress urinary incontinence, said treatment comprising surgical implantation of the porous biomedical implant as defined hereinbefore or obtainable by the electro-spinning process as defined hereinbefore at the site of a mammalian subject that needs reconstruction surgery, support or augmentation, wherein the porous biomedical implant acts as a scaffold for the formation of new tissue.

In a preferred embodiment the porous biomedical implant as defined hereinbefore or obtainable by the electro-spinning process as defined hereinbefore for use in the treatment of a medical condition requiring reconstruction surgery, support or augmentation has the form of a sheet comprising 0 to 6 arms or extensions for attachment to structures in the site of the implantation.

In an embodiment the porous biomedical implants comprising the supramolecular biomedical polymer are used for ligaments reconstructions.

The porous biomedical implants comprising the supramolecular biomedical polymer may be delivered to the patient by any surgical procedure, including minimally invasive techniques, such as endoscopic or laparoscopic surgery, as well as invasive techniques such as thoracic surgery or open-heart surgery.

Thus, the invention has been described by reference to certain embodiments discussed above. It will be recognized that these embodiments are susceptible to various modifications and alternative forms well known to those of skill in the art.

Furthermore, for a proper understanding of this document and its claims, it is to be understood that the verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

EXAMPLES

The following examples further illustrate the preferred embodiments of the invention. When not specifically mentioned, chemicals are obtained from Sigma-Aldrich or Merck. The number average molecular weight $M_n$ of functionalized polymer A' has been determined from its hydroxyl value.

Example 1: Preparation of 5-(2-hydroxyethyl)-6-methyl-isocytosine

2-Acetylbutyrolactone (2.38 g, 19 mmol) and guanidine carbonate (3.3 g, 37 mmol) were put to reflux in absolute ethanol (20 mL) in the presence of triethylamine (5.2 mL). The solution became yellow and turbid. After overnight heating at reflux, the solid was filtered, washed with ethanol, and suspended in water. The pH was adjusted to a value of 6-7 with an HCl-solution, and the mixture was stirred for a while. Filtration, rinsing of the residue with water and ethanol and subsequent drying of the solid gave the pure 5-(2-hydroxyethyl)-6-methyl-isocytosine. $^1$H NMR (400 MHz, DMSO-d6): δ 11.2 (1H), 6.6 (2H), 4.5 (1H), 3.4 (2H), 2.5 (2H), 2.1 (3H). FT-IR (neat): ν (cm$^{-1}$) 3333, 3073, 2871, 1639, 1609, 1541, 1487, 1393, 1233, 1051, 915, 853, 789, 716.

Example 2: Preparation of 5-(4-hydroxybutyl)-6-methyl-isocytosine

2(i) Preparation of 2-(4-chlorobutoxy)tetrahydro-2H-pyran 4-chlorobutan-1-ol (24 g, 220 mmol) and dihydropyran (22.3 g, 270 mmol) were dissolved in dichloromethane and pyridinium p-toluenesulfonate (5.2 g, 18 mmol) was added. The slightly cloudy solution was stirred overnight at room temperature yielding a brownish solution which was washed twice with water and dried with sodium sulfate. Evaporation of the solvent yielded the crude product which was purified by vacuum distillation (70° C., 0.08 mbar) giving 35.5 g of a colorless oil (83%).

2(ii) Preparation of 2-(4-iodobutoxy)tetrahydro-2H-pyran 2-(4-chlorobutoxy)tetrahydro-2H-pyran (33.5 g, 170 mmol, from step 2(i)), sodium iodide (78 g, 520 mmol) and sodium carbonate (11 g, 100 mmol) were refluxed for 56 hours in 800 mL of acetone. Then, the mixture was concentrated and poured into 1 l of a saturated sodium bicarbonate solution. The aqueous solution was three times extracted with hexane and the combined organic layers were washed with brine and dried over sodium sulfate. Evaporation of the solvent yielded 44.5 g (90%) of the pure product.

2(iii) Preparation of ethyl 2-acetyl-6-((tetrahydro-2H-pyran-2-yl)oxy)hexanoate

To a mixture of ethyl acetoacetate (24.1 g, 185 mmol) and potassium carbonate (35.4 g, 226 mmol) in acetone (300 mL) and DMF (60 mL) was added dropwise a solution of 2-(4-iodobutoxy)tetrahydro-2H-pyran (40.4 g, 142 mmol, from step 2(ii)) in acetone (300 mL). This mixture was stirred for 64 hours at room temperature after which it was concentrated and partitioned between ethyl acetate and a saturated ammonium chloride solution. The aqueous phase was extracted with ethyl acetate and the combined ethyl acetate layers were washed with a 10% aqueous solution of sodium thiosulfate, brine and dried over sodium sulfate. Evaporation of the solvent yielded 54 g of the crude product which was used without further purification.

2(iv) Preparation of 2-amino-6-methyl-5-(4-((tetrahydro-2H-pyran-2-yl)oxy)butyl) pyrimidin-4(1H)-one A mixture of ethyl 2-acetyl-6-((tetrahydro-2H-pyran-2-yl)oxy)hexanoate (40.7 g, 140 mmol, from step 2(iii)) and guanidine carbonate (27.5 g, 143 mmol) in ethanol (800 mL) was refluxed for 80 hours. The mixture was concentrated to approximately 100 mL and 800 mL of chloroform was added. The lightly turbid solution was washed with a sodium bicarbonate solution, brine and dried over sodium sulfate. After evaporation of the solvent the resulting solid was stirred overnight in diethyl ether. Filtration, washing with diethyl ether and drying in vacuum yielded 28 g (70%) of the pure product as white solid.

2(v) Preparation of 5-(4-hydroxybutyl)-6-methyl-isocytosine 2-amino-6-methyl-5-(4-((tetrahydro-2H-pyran-2-yl)oxy) butyl)pyrimidin-4(1H)-one (28 g, 100 mmol, from step 2(iv)) and p-toluenesulfonic acid (20.8 g, 109 mmol) were stirred at 60° C. for 3 hours in 500 mL of methanol. The solvent was evaporated and the resulting white solid was neutralized by stirring in 120 mL of a saturated sodium bicarbonate solution. The solid was filtered of, washed with water and triturated two times with diethyl ether. Drying in vacuum above phosphorus pentoxide gave 18 g (92%) of 5-(4-hydroxybutyl)-6-methyl-isocytosine as a white solid.

$^1$H NMR (399 MHz, DMSO) δ 10.88 (1H), 6.29 (2H), 4.32 (1H), 3.39 (1H), 3.37 (2H), 2.25 (2H), 2.03 (3H), 1.39 (4H). LC-MS: m/z=198 [M+1]. FT-IR (neat): ν (cm$^{-1}$) 3273, 3100, 2932, 1688, 1601, 1504, 1375, 1231, 1053, 974, 862, 806, 777

Example 3: Preparation of 5-(4-aminobutyl)-6-methyl-isocytosine

3(i) Preparation of tert-butyl (4-iodobutyl)carbamate

Iodine (80.5 g, 320 mmol) was added portion wise to a solution of triphenylphosphine (83.2 g, 320 mmol) and imidazole (21.6 g, 320 mmol) in dichloromethane (1.5 L) at 0° C. The orange mixture was allowed to warm up to room temperature after which tert-butyl (4-hydroxybutyl)carbamate (50 g, 260 mmol) diluted in dichloromethane (300 mL) was slowly added. After 3 hours stirring at room temperature the mixture was filtered over celite and rinsed with dichloromethane. The orange filtrate was washed twice with a 5% sodium thiosulfate solution yielding a colorless organic layer which was dried with magnesium sulfate. The solvent was evacuated in vacuum and the resulting solid was thoroughly stirred overnight in 2 L of a 3:1 mixture of heptane and diethyl ether. After filtration and washing with the same mixture of solvents, the filtrate was concentrated to give the crude product as a yellow oil. Purification was performed by column chromatography eluting over silica with ethyl acetate: heptane (1:9) yielding 56 g (71%) of a yellow oil.

3(ii) Preparation of ethyl 2-acetyl-6-((tert-butoxycarbonyl)amino)hexanoate

To a mixture of ethyl 3-oxobutanoate (28 g, 220 mmol, from step 3(i)) and potassium carbonate (36 g, 260 mmol) in acetone (250 mL) and DMF (40 mL) was added dropwise a solution of tert-butyl (4-iodobutyl)carbamate (50 g, 170 mmol) in acetone (250 mL). This mixture was stirred for 20 hours at room temperature after which it was concentrated and partitioned between ethyl acetate and a saturated ammonium chloride solution. The ethyl acetate layer was washed with brine and dried with sodium sulfate. Evaporation of the solvent yielded a yellow oil (54 g). This crude product was used without further purification.

3(iii) Preparation of tert-butyl (4-(2-amino-6-methyl-4-oxo-1,4-dihydropyrimidin-5-yl)butyl)carbamate A mixture of ethyl 2-acetyl-6-((tert-butoxycarbonyl) amino)hexanoate (54 g, 179 mmol, from step 3(ii)) and guanidine carbonate (27.5 g, 143 mmol) in ethanol (800 mL) was refluxed for 24 hours. The clear solution was concentrated to 300 mL and diluted with 300 mL of water. The pH was adjusted to a value of 5.8 with a hydrochloride solution. The precipitate was filtered off and washed with water. The residue was triturated with diethyl ether and dried at 40° C. under reduced pressure yielding 33.5 g (63%) of the pure product as a white solid.

3(iv) Preparation of 5-(4-aminobutyl)-6-methyl-isocytosine

A mixture of tert-butyl (4-(2-amino-6-methyl-4-oxo-1,4-dihydropyrimidin-5-yl)butyl)carbamate (30 g, 101 mmol, from step 3(iii)) in dichloromethane (300 mL) was stirred and cooled to 0° C. Trifluoroacetic acid (62 mL, 810 mmol) was added dropwise resulting in a clear solution which was stirred at room temperature for 4 hours. The solvent and excess of trifluoroacetic acid were removed by evaporation and coevaporation with methanol yielding the trifluoroacetic acid salt of the product as a white solid. This solid was dissolved in 300 mL of methanol and cooled to 0° C. after which an excess of N,N-di-isopropylethylamine was added. After stirring for a couple of hours the mixture was filtered and the residue washed with methanol. The residue was stirred in methanol with an excess of N,N-di-isopropylethylamine. After filtration the residue was stirred in chloroform overnight. Filtration and drying of the residue gave 15.4 g (77%) of 5-(4-aminobutyl)-6-methyl-isocytosine. $^1$H NMR (400 MHz, D$_2$O) δ 2.77 (2H), 2.27 (2H), 2.03 (3H), 1.49 (2H), 1.32 (2H). LC-MS: m/z=197 [M+1]. FT-IR (neat): ν (cm$^{-1}$) 3061, 2963, 2918, 2845, 1692, 1628, 1586, 1372, 1233, 1140, 974, 951, 885, 802, 698.

Example 4: Preparation of 5-(11-undecyl)-6-methyl-isocytosine

4(i) Preparation of ethyl 2-acetyl-13-hydroxytridecanoate

Ethyl acetoacetate (16.8 g, 130 mmol) dissolved in 30 mL of acetone was added to a mixture of potassium carbonate (27.5 g, 200 mmol) and potassium iodide (1.65 g, 10 mmol) in 350 mL of acetone and 50 mL of DMF at 60° C. To the resulting mixture, stirred at 60° C., was added dropwise a solution of 1-bromo-1-undecanol (25 g, 100 mmol) in 100 mL of acetone. After refluxing overnight the mixture was cooled to room temperature and the precipitate was filtered off. The filtrate was evaporated till dryness, dissolved in ethyl acetate and washed twice with a half saturated aqueous solution of ammonium chloride and once with brine. After drying over sodium sulfate the solvent was evaporated yielding 32.6 g of the crude product which was used without further purification.

4(ii) Preparation of 5-(11-undecyl)-6-methyl-isocytosine

A mixture of ethyl 2-acetyl-13-hydroxytridecanoate (30 g, 100 mmol, from step 4(i)) and guanidine carbonate (14.4 g, 80 mmol) in ethanol (400 mL) was refluxed for 48 hours. After cooling to room temperature the precipitate was filtered off and the filtrate was evaporated till dryness. The resulting slurry was stirred in 600 mL of a half saturated aqueous solution of sodium bicarbonate. After filtration the residue was triturated with respectively water and diethyl ether. Drying of the residue under vacuum above phosphorus pentoxide gave 19.8 g (67%) of the product as a white solid. This was further purified by respectively precipitation from DMSO in water and trituration with ethanol, resulting in 5-(11-undecyl)-6-methyl-isocytosine. $^1$H NMR (400 MHz, DMSO) δ 10.80 (1H), 6.28 (2H), 4.31 (1H), 3.37 (2H), 2.23 (2H), 2.02 (3H), 1.39 (2H), 1.24 (16H). LC-MS: m/z=296 [M+1]. FT-IR (neat): ν (cm$^{-1}$) 3316, 3127, 2916, 2849, 1682, 1602, 1381, 1244, 1142, 1051, 1034, 980, 872, 808, 779.

Example 5: Preparation of Polymer 1

Telechelic hydroxy terminated poly(1,6-hexanediol) carbonate with a molecular weight of 1000 Da (20.0 g, 20.0 mmol, dried in vacuo, functionalized Polymer A'), the isocytosine monomer obtained in Example 1 (3.38 g, 20.0 mmol, Compound F'), 1,6-hexanediol (4.72 g, 40.0 mmol, dried in vacuo, Compound B'), hexamethylene diisocyanate (13.31 g, 79.2 mmol, Compound C') and two drops of catalyst tin dioctoate were dissolved in dry DMSO (40 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and reprecipitated in an excess of methanol. This resulted in a clear elastic solid after drying in vacuo at 50° C. SEC (DMF, 10 mM LiBr, PEO/PEG-standards): $M_n$=14.6 kDa, $Mw/M_n$=1.9.

Example 6: Preparation of Polymer 2

Telechelic hydroxy terminated poly(1,6-hexanediol) carbonate with a molecular weight of 1000 Da (20.0 g, 20.0 mmol, dried in vacuo, functionalized Polymer A'), the isocytosine monomer obtained in Example 1 (3.38 g, 20.0 mmol, Compound F'), 1,6-hexanediol (3.54 g, 30.0 mmol, dried in vacuo, Compound B'), hexamethylene diisocyanate (11.64 g, 69.3 mmol, Compound C') and two drops of catalyst tin dioctoate were dissolved in dry DMSO (30 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and reprecipitated in an excess of methanol. This resulted in a clear elastic solid after drying in vacuo at 50° C. SEC (DMF, 10 mM LiBr, PEO/PEG-standards): $M_n$=18.6 kDa, $Mw/M_n$=1.9.

Example 7: Preparation of Polymer 3

Telechelic hydroxy terminated poly(1,6-hexanediol) carbonate with a molecular weight of 1000 Da (20.0 g, 20.0 mmol, dried in vacuo, functionalized Polymer A'), 5-(11-undecyl)-6-methyl-isocytosine (5.90 g, 20.0 mmol, Compound F'), 1,6-hexanediol (4.72 g, 40.0 mmol, dried in vacuo, Compound B'), hexamethylene diisocyanate (13.31 g, 79.2 mmol, Compound C') and two drops of catalyst tin dioctoate were dissolved in dry DMSO (20 mL) and stirred at 80° C. The next day the reaction mixture was cooled to 25° C. and its viscosity was lowered by the addition of additional DMSO and the resulting mixture was added to an excess of water in order to precipitate the polymer. The polymer was collected as a white elastic solid, was redissolved in chloroform/methanol (7/3 v/v) and reprecipitated in an excess of methanol. This resulted in a clear elastic solid after drying in vacuo at 50° C. SEC (DMF, 10 mM LiBr, PEO/PEG-standards): $M_n$=14.0 kDa, $Mw/M_n$=2.1.

Example 8: Preparation of Polymer 4

Telechelic hydroxy terminated poly(tetramethylene ether) glycol with a molecular weight of 1000 Da (40.0 g, 40.0 mmol, dried in vacuo, functionalized Polymer A'), the isocytosine monomer obtained in Example 1 (6.76 g, 40.0 mmol, Compound F'), 1,6-hexanediol (9.44 g, 80.0 mmol, dried in vacuo, Compound B'), hexamethylene diisocyanate (26.61 g, 158.4 mmol, Compound C') and three drops of catalyst tin dioctoate were dissolved in dry DMSO (60 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=16.5 kDa, Mw/$M_n$=1.9.

Example 9: Preparation of Polymer 5

Telechelic hydroxy terminated poly(1,6-hexanediol) carbonate with a molecular weight of 1000 Da (20.0 g, 20.0 mmol, dried in vacuo, functionalized Polymer A'), the isocytosine monomer obtained in Example 1 (3.38 g, 20.0 mmol, Compound F'), 1,4-butanediol (3.60 g, 40.0 mmol, dried in vacuo, Compound B'), butylene diisocyanate (11.09 g, 79.2 mmol, Compound C') and two drops of catalyst tin dioctoate were dissolved in dry DMSO (30 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=14.0 kDa, Mw/$M_n$=1.8.

Comparative Example 1: Preparation of Polymer C1 in which A':B':C':F' is 1:1:3:1

Telechelic hydroxy terminated poly(1,6-hexanediol) carbonate with a molecular weight of 1000 Da (20.0 g, 20.0 mmol, dried in vacuo, functionalized Polymer A'), the isocytosine monomer obtained in Example 1 (3.38 g, 20.0 mmol, Compound F'), 1,6-hexanediol (2.36 g, 20.0 mmol, dried in vacuo, Compound B'), hexamethylene diisocyanate (10.69 g, 59.4 mmol, Compound C') and two drops of catalyst tin dioctoate were dissolved in dry DMSO (20 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=13.2 kDa, Mw/Mn=2.1.

Comparative Example 2: Preparation of Polymer C2 in which A':B':C':F' is 1:2.5:4.5:1

Telechelic hydroxy terminated poly(1,6-hexanediol) carbonate with a molecular weight of 1000 Da (20.0 g, 20.0 mmol, dried in vacuo, functionalized Polymer A'), the isocytosine monomer obtained in Example 1 (3.38 g, 20.0 mmol, Compound F'), 1,6-hexanediol (5.90 g, 50.0 mmol, dried in vacuo, Compound B'), hexamethylene diisocyanate (14.97 g, 89.1 mmol, Compound C') and two drops of catalyst tin dioctoate were dissolved in dry DMSO (40 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=18.4 kDa, Mw/Mn=1.8.

Comparative Example 3: Preparation of Polymer C3 in which Polymer A' is a Polycarbonate with $M_n$=3000

Telechelic hydroxy terminated poly(1,6-hexanediol) carbonate with a molecular weight of 3000 Da (30.0 g, 10.0 mmol, dried in vacuo, functionalized Polymer A'), the isocytosine monomer obtained in Example 1 (1.69 g, 10.0 mmol, Compound F'), 1,6-hexanediol (2.36 g, 20.0 mmol, dried in vacuo, Compound B'), hexamethylene diisocyanate (6.65 g, 39.6 mmol, Compound C') and two drops of catalyst tin dioctoate were dissolved in dry DMSO (30 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=15.1 kDa, Mw/Mn=1.8.

Comparative Example 4: Preparation of Polymer C4 in which Polymer A' is a Polycarbonate with $M_n$=500

Telechelic hydroxy terminated poly(1,6-hexanediol) carbonate with a molecular weight of 500 Da (20.0 g, 40.0 mmol, dried in vacuo, Polymer A'), the isocytosine monomer obtained in Example 1 (6.76 g, 40.0 mmol, Compound F'), 1,6-hexanediol (9.44 g, 80.0 mmol, dried in vacuo, Compound B'), hexamethylene diisocyanate (26.61 g, 158.4 mmol, Compound C') and three drops of catalyst tin dioctoate were dissolved in dry DMSO (40 mL) and stirred at 80° C. The next day the reaction mixture was cooled to 25° C., its viscosity was lowered by the addition of additional DMSO and the resulting mixture was added to an excess of water in order to precipitate the polymer. The polymer was collected as a white elastic solid, was redissolved in chloroform/methanol (7/3 v/v) and repreciptated in an excess of methanol. This resulted in a clear elastic solid after drying in vacuo at 50° C. SEC (DMF, 10 mM LiBr, PEO/PEG-standards): $M_n$=16.2 kDa, Mw/Mn=2.1.

Comparative Example 5: Preparation of Polymer C5 in which Polymer A' is a Polycaprolactone with $M_n$=2000

Telechelic hydroxy terminated polycaprolactone with a molecular weight of 2000 Da (20.4 g, 10 mmol, dried in vacuo, functionalized Polymer A') and hexamethylene diisocyanate (6.85 g, 40 mmol, Compound C') were stirred together at 80° C. in the presence of one drop of catalyst tin dioctoate for 2 hours. To this reaction mixture was subsequently added the isocytosine monomer obtained in Example 1 (1.72 g, 10 mmol, Compound F') dissolved in dry DMSO (120 mL) and stirred overnight at 80° C. The next day, 1,6-hexanediol (2.34 g, 20 mmol, dried in vacuo, Compound B') was added to the reaction mixture, followed by stirring for another 2 hours at 80° C. The reaction mixture was cooled to 25° C., its viscosity was lowered by the addition of additional DMSO and the resulting mixture was added to an excess of water in order to precipitate the polymer. The polymer was collected as white elastic solid, redissolved in chloroform/methanol (7/3 v/v) and reprecipitated in an excess methanol. This resulted in a clear elastic solid after drying in vacuo at 50° C. SEC (DMF, 10 mM LiBr, PEO/PEG-standards): Mn=20.3 kDa, Mw/Mn=2.1.

Example 9: Thermal and Mechanical Properties

The following tables show the superior thermal and mechanical properties of the polymers according to this invention when compared to the state of the art. All measurements have been performed on films, or parts of films, that have been obtained from solvent casting and that showed no visible defects such as blisters. Moreover, all films have been aged for 2 weeks at room temperature before testing.

TABLE 1

Thermal transitions of the Polymers of the Examples above 0° C.

| Polymer No | $T_g$ (° C.) | $T_{m1}$ (° C.) | $T_{m2}$ (° C.) |
|---|---|---|---|
| 1 | — | 57 | 119 |
| 2 | — | 62 | 113 |
| 3 | — | 65 | 125 |
| 4 | — | 71 | 119 |
| 5 | — | 80 | 137 |
| C1 | — | 72 | 111, 135 |
| C2 | — | 61 | 125 |
| C3 | — | 13 | 58, 117 |
| C4 | — | 61 | 124 |
| C5 | — | 53 | 116 |

Thermal data were obtained using Differential Scanning calorimetry (DSC) with a heating rate of 20° C./min and a heating range from −80° C. to 160° C. Data are based on the first heating runs.

TABLE 2

Mechanical data of the Polymers of the Examples

| Polymer No | $E_{mod}$ (MPa) | $E_{100\%}$ (MPa) | Ultimate Tensile strength (MPa) | Elongation at break |
|---|---|---|---|---|
| 1 | 150 | 17 | 42 | 480% |
| 2 | 55 | 13 | 62 | 420% |
| 3 | 159 | 15 | 38 | 425% |
| 4 | 55 | 8 | 38 | 540% |
| 5 | 130 | 15 | 48 | 390% |
| C1 | 21 | 7.5 | 62 | 440% |
| C2 | 185 | 18 | 47 | 470% |
| C3 | 38 | 6 | 34 | 560% |
| C4 | 250 | 23 | 50 | 380% |
| C5 | 30 | 6 | 16 | 470% |

Tensile testing was performed on dog bones cut from solvent casted films according to ASTM D1708-96 specifications in air at a temperature of 23±2° C. with an elongation rate of 20 mm/min and a preload of 0.02 N. Young's moduli were measured between 0.25 and 2.50% elongation.

TABLE 3

Fatigue test

| Polymer No | number of cycles without failure |
|---|---|
| 1 | >3 × 10⁶ |
| 2 | >3 × 10⁶ |
| C5 | <1 × 10⁵ |

Fatigue testing was performed on a strip of solvent casted polymer film of 5×25 mm with a thickness in between 0.2 and 0.5 mm in air at a temperature of 23±2° C. using a uniaxial tensile tester with an elongation of 10% at a sample rate of 10 Hz, whereby fatigue failure is defined at the cycle in which the stress response is below 10% of the stress response at the first cycle.

Example 10: Electro-Spinning

Polymer 3 of Example 8 was dissolved in chloroform/hexafluoropropanol (80/20) at a concentration of 14 wt %. The resulting solution had a viscosity high enough to allow stable electro-spinning of the solution with the desired fibre thicknesses. The resulting non-woven mesh structure could be further used as scaffold material for tissue engineering. Electro-spinning was performed at 12 kV, 0.025 mL/min, and a tip-to-target distance of 15 cm. Fibers were deposited on a static, grounded collector plate that was covered with a polyethylene film to enable facile removal of the electrospun scaffold. Subsequently, the scaffolds were dried in vacuo at 40° C. for 24 h to remove any residual solvent.

The invention claimed is:

1. A process for the manufacture of a supramolecular biomedical polymer for porous biomedical implants, wherein the supramolecular biomedical polymer has an ultimate tensile strength of at least 35 MPa, a Young's modulus of between 40 and 160 MPa, and an elongation at break of at least 350%, as determined by test method ASTM D 1708-96 with a crosshead speed of 20 mm/min, the process comprising reacting a compound F' according to Formula (1):

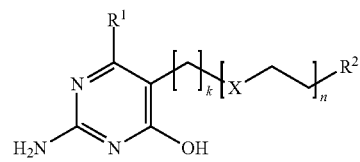

(1)

with:
a diisocyanate compound C' according to the Formula O=C=N—R³—N=C=O;
a functionalized polymer A' according to the Formula P-(FG1)$_w$; and
a compound B' according to the Formula FG2-R⁴-FG3;
wherein:
X is O or S;
k is an integer of 1 to 20;
n is an integer of 0 to 8;
R¹ is a C₁-C₁₃ alkyl group;
R² is a functional group selected from OH, SH and NH₂;
FG1, FG2 and FG3 are functional groups independently selected from OH and NH₂;
w is in the range of about 1.8 to about 2;
functionalized polymer A' has a number average molecular weight $M_n$, as determined from its hydroxyl value, of about 1000 to about 2000 Da, and is selected from hydroxy terminated poly(1,6-hexanediol) carbonate, poly(tetramethylene glycol), and FG1-functionalized hydrogenated polybutadiene;
R³ is a linear C₄-C₂₀ alkylene group;
R⁴ is a linear C₂-C₂₀ alkylene group; and wherein the molar ratio of compounds A', B', C' and F' expressed as A':B':C':F' is between 1:1.5:3.5:1 and 1:2:4:1.

2. The process according to claim 1, wherein the reaction is performed in one step.

3. The process according to claim 1, wherein $R^1$ is methyl and:
(a) k is 2, n is 0, and $R^2$ is OH;
(b) k is 2, n is 1,$R^2$ is OH and X is O;
(c) k is 4 to 11, n is 0,$R^2$ is OH; or
(d) k is 4 to 11, n is 0,$R^2$ is $NH_2$.

4. The process according to claim 1, wherein functionalized polymer A' is hydroxy terminated poly(1,6-hexanediol) carbonate, and FG1 is OH.

5. The process according to claim 1, wherein compound B' is selected from the group consisting of 1,4-butanediol, 1,12-dodecyldiol and 1,6-hexanediol.

6. The process according to claim 1, wherein compound B' is 1,6-hexanediol.

7. The process according to claim 1, wherein diisocyanate compound C' is selected from the group consisting of 1,4-diisocyanatobutane, 1,6-diisocyanatohexane (HDI) and 1,12-diisocyanatododecane.

8. The process according to claim 1, wherein diisocyanate compound C' is 1,6-diisocyanatohexane.

9. A supramolecular biomedical polymer for porous biomedical implants, wherein the supramolecular biomedical polymer has an ultimate tensile strength of at least 35 MPa, a Young's modulus of between 40 and 160 MPa, and an elongation at break of at least 350%, as determined by test method ASTM D 1708-96 with a crosshead speed of 20 mm/min, obtainable by the process according to claim 1.

10. The supramolecular biomedical polymer according to claim 9, having a number average molecular weight $M_n$ of about 3000 to about 150000 Da as determined with size-exclusion chromatography in DMF comprising 10 mM LiBr at 50° C. using PEO/PEG-standards.

11. The supramolecular biomedical polymer according to claim 9, having at least one of the following properties:
(i) a modulus at 100% elongation of at least 7 MPa, as determined by test method ASTM D 1708-96, with a crosshead speed of 20 mm/min;
(ii) an ultimate tensile strength of at least 40 MPa, as determined by test method ASTM D 1708-96 with a crosshead speed of 20 mm/min;
(iii) a fatigue resistance of at least 3 million cycles before failure, as determined on a strip of polymer of 5×25 mm with a thickness in between 0.2 and 1 mm using a uniaxial tensile tester with an elongation of 10% at a sample rate of 10 Hz, whereby fatigue failure is defined at the cycle in which the stress response is below 10% of the stress response at the first cycle; and
(iv) at least two thermal transitions selected from glass transitions and melting points at a temperature between 50 and 125° C. and no thermal transition in between 0 and 45° C., as determined with differential scanning calorimetry at a heating rate of 20° C./min.

12. The supramolecular biomedical polymer according to claim 11, having all of the properties (i) to (iv).

13. A porous biomedical implant comprising the supramolecular biomedical polymer according to claim 9.

14. The porous biomedical implant according to claim 13, comprising 1 to 3 leaflet structures.

15. The porous biomedical implant according to claim 13, having a non-woven mesh structure obtained by electro-spinning the supramolecular biomedical polymer from solution.

16. The porous biomedical implant according to claim 13, in the form of a sheet comprising 0 to 6 arms or extensions for attachment to structures in the site of the implantation.

17. A process for the manufacture of a porous biomedical implant having a non-woven mesh structure comprising the supramolecular biomedical polymer, the process comprising:
(a) providing the supramolecular biomedical polymer having an ultimate tensile strength of at least 35 MPa, a Young's modulus of between 40 and 160 MPa, and an elongation at break of at least 350%, as determined by test method ASTM D 1708-96 with a crosshead speed of 20 mm/min, obtainable by the process according to claim 1;
(b) dissolving the supramolecular biomedical polymer in a solvent mixture suitable for electro-spinning;
(c) electro-spinning the polymer solution from (b) on a target; and
(d) isolating the porous biomedical implant from the target as a sheet, cylinder, or complex 3D-structure.

18. The supramolecular biomedical polymer according to claim 1, having an ultimate tensile strength of at least 40 MPa.

19. The supramolecular biomedical polymer according to claim 1, wherein the functionalized polymer A' does not comprise polycaprolactone or polyethylene glycol.

* * * * *